(12) United States Patent
Blanchard et al.

(10) Patent No.: US 11,495,359 B2
(45) Date of Patent: Nov. 8, 2022

(54) SYSTEMS AND METHODS FOR IDENTIFYING RISK OF INFECTION IN DIALYSIS PATIENTS

(71) Applicant: Fresenius Medical Care Holdings, Inc., Waltham, MA (US)

(72) Inventors: Thomas C. Blanchard, Somerville, MA (US); Len Usvyat, Boston, MA (US); Joanna L. Willetts, Framingham, MA (US); Melissa C. Herman, Ladson, SC (US); Brian C. Ellison, Atlanta, GA (US); Judith E. Moran, Somerset, NJ (US); Dinesh K. Chatoth, Suwanee, GA (US)

(73) Assignee: FRESENIUS MEDICAL CARE HOLDINGS, INC., Waltham, MA (US)

( * ) Notice: Subject to any disclaimer, the term of this patent is extended or adjusted under 35 U.S.C. 154(b) by 173 days.

(21) Appl. No.: 16/456,510

(22) Filed: Jun. 28, 2019

(65) Prior Publication Data

US 2020/0005947 A1    Jan. 2, 2020

Related U.S. Application Data

(60) Provisional application No. 62/836,822, filed on Apr. 22, 2019, provisional application No. 62/716,031, filed on Aug. 8, 2018, provisional application No. 62/692,198, filed on Jun. 29, 2018.

(51) Int. Cl.
*G16H 50/70* (2018.01)
*G16H 15/00* (2018.01)
(Continued)

(52) U.S. Cl.
CPC .......... *G16H 50/70* (2018.01); *G16H 10/20* (2018.01); *G16H 15/00* (2018.01); *G16H 50/30* (2018.01)

(58) Field of Classification Search
None
See application file for complete search history.

(56) References Cited

U.S. PATENT DOCUMENTS

2015/0220699 A1 *  8/2015  Ostrovsky ............. G06Q 10/10 705/2
2016/0239611 A1 *  8/2016  Heldt ..................... A61B 5/412
(Continued)

FOREIGN PATENT DOCUMENTS

WO      2017177111 A1      10/2017
WO   WO-2017194735 A1 *  11/2017  ............ C12Q 1/689

OTHER PUBLICATIONS

Shepshelovich, et al., "Chills During Hemodialysis: Prediction and Prevalence of Bacterial Infections—A Retrospective Cohort Study," The American Journal of Medicine, Apr. 2017, vol. 130, Issue 4, pp. 477-481 (Year: 2017).*

(Continued)

*Primary Examiner* — Rachel L. Porter
(74) *Attorney, Agent, or Firm* — Seager, Tufte & Wickhem, LLP

(57) ABSTRACT

A method and system for determining a patient's risk of developing an infection is disclosed. In one embodiment, the system and method includes extracting patient data from one or more databases corresponding to a pool of patients receiving treatment; using one or more predictive models with the extracted patient data to generate, for each of the patients in the pool of patients, a respective patient risk score for developing an infection within a selected time period; generating a report including at least a portion of the identified subset of the pool of patients and their respective patient risk scores; and transmitting the report to one or more health care facilities, the one or more health care facilities further identifying one or more patients from the portion of the identified subset of the pool of patients for interventional treatment, consultation, training, or combinations thereof.

28 Claims, 20 Drawing Sheets

(51) Int. Cl.
   *G16H 50/30* (2018.01)
   *G16H 10/20* (2018.01)

(56) References Cited

U.S. PATENT DOCUMENTS

2016/0283686 A1    9/2016   Hu et al.
2016/0357923 A1*   12/2016   Dong ................... G16H 50/20

OTHER PUBLICATIONS

Chang YJ, Yeh ML, Li YC, Hsu CY, Lin CO, Hsu MS, Chiu WT. Predicting hospital-acquired infections by scoring system with simple parameters. PLoS One. 2011;6(8):. (Epub Aug. 24, 2011).11 pages (Year: 2011).*

International Search Report and Written Opinion for International application No. PCT/US2019/039786, dated Oct. 25, 2019, 13 pages.

Shepshelovich, D., et al., "Chills During Hemodialysis: Prediction and Prevalence of Bacterial Infections—A Retrospective Cohort Study", American Journal of Medicine,130(4):477-481 (2016) abstract.

Kumar, V.A., "Predictors of Peritonitis, Hospital Days, and Technique Survival for Peritoneal Dialysis Patients in a Managed Care Setting", Peritoneal Dialysis International 34(2):171-178 (2013).

Campos-Lobato, L.F., et al., "Predicting Organ Space Surgical Site Infection with a Nomogram", Journal of Gastrointstinal Surgery 13(11): 1986-1992 (2009) abstract.

* cited by examiner

| Variables | Description |
|---|---|
| # of Days on Home Dialysis | Time of patient receiving at-home dialysis treatments |
| # of Days Since Previous Infection | Time between infections |
| Average Albumin levels | Patient Albumin levels averaged over a predetermined period of time |
| Standard Deviation of Albumin levels | Standard deviation of patient albumin levels |
| Average Calcium levels | Patient Calcium levels averaged over a predetermined period of time |
| Standard Deviation of Calcium levels | Standard deviation of patient calcium levels |
| Average Creatinine levels | Patient Creatinine levels averaged over a predetermined period of time |
| Standard Deviation of Creatinine levels | Standard deviation of patient creatinine levels |
| Average Transferrin Saturation | Patient stored iron for new red blood cells |
| # of Previous Infections | Total number of previous infections of a patient |
| Distance of patient from facility | Distance from patient's home to dialysis facility |
| Patient demographics | Patient gender, race, date of birth, marital status |

FIG. 1B

| Patient First Name | Patient Last Name | Patient DOB | MRN | Clinic ID | Risk score for developing infection in next month | Reason 1 | Reason 2 | Reason 3 | Reason 4 | Reason 5 |
|---|---|---|---|---|---|---|---|---|---|---|
| John | Smith | MM/DD/YYYY | 12345 | 98765 | 82.67 | Albumin: 2.40 | Chloride: 98.00 | TSAT Mean: 26.90 | Days since infection: 45.00 | KCCreat_90_MEAN_DIFF: 0.34 |
| Jane | Doe | MM/DD/YYYY | 12345 | 98765 | 81.75 | Days since infection: 37.00 | Creatinine: N/A | Calcium Mean: 8.45 | Chloride: 93.00 | Creat_180_STD: 0.41 |

FIG. 1C

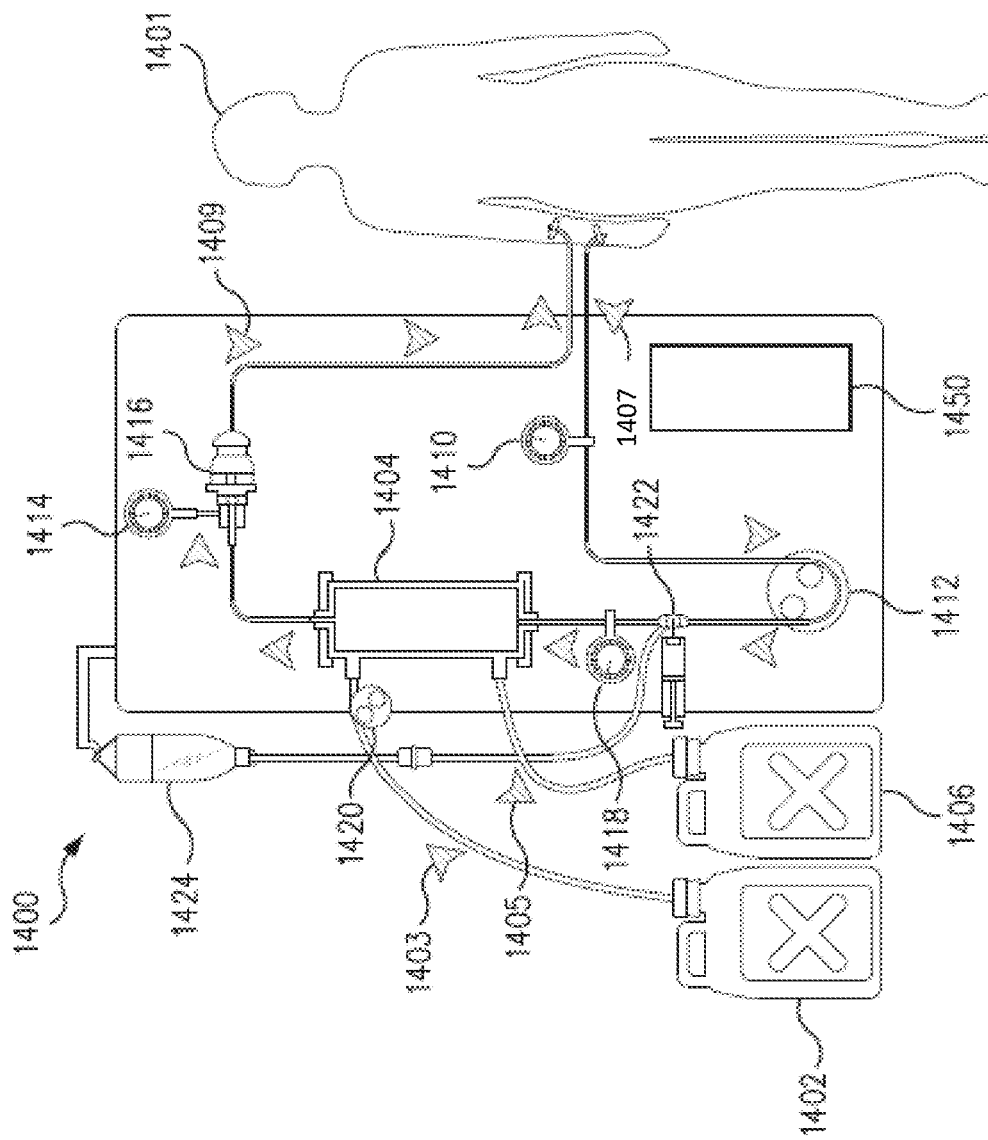

SYSTEMS AND METHODS FOR IDENTIFYING RISK OF INFECTION IN DIALYSIS PATIENTS

CROSS-REFERENCE TO RELATED APPLICATIONS

This is a non-provisional of, and claims the benefit of the filing date of, U.S. provisional patent application No. 62/692,198, filed Jun. 29, 2018, entitled "Systems and Methods for Identifying Risk of Infection in Dialysis Patients," is a non-provisional of, and claims the benefit of the filing date of, U.S. provisional patent application No. 62/716,031, filed Aug. 8, 2018, entitled "Systems and Methods for Identifying Risk of Infection in Dialysis Patients," and is a non-provisional of, and claims the benefit of the filing date of, U.S. provisional patent application No. 62/836,822, filed Apr. 22, 2019, entitled "Artificial Intelligence & Predictive Medicine in Dialysis," the entirety of which applications are expressly incorporated by reference herein.

FIELD

The disclosure generally relates to healthcare related systems, devices, and methods.

BACKGROUND

Traditional health care systems are based on a fee-for-service model, whereby healthcare providers are compensated on a per-treatment or per-service basis. Under this model, a healthcare provider's compensation increases when the number of provided treatments or services increases. As such, there is no financial incentive for such providers to efficiently manage the number of provided services/procedures, nor is there any financial incentive related to the overall health outcome of the patient. Such traditional systems have led to spiraling healthcare costs and inefficiencies hindering the quality of overall care of the patient.

Moreover, many patients—especially patients with chronic illnesses—engage with a variety of different entities and health care professionals in the course of their diagnosis, treatment, and long-term care management, including hospitals, clinics, laboratories, pharmacies, physicians, clinicians, and/or other specialists. The patients' treatment information may be spread across several entities, repositories, and medical professionals, which can lead to lack of communication, or miscommunication, between the various involved entities, which can detrimentally affect the treatment and health of the patient, possibly even creating life-threatening treatment conditions. Further, this uncoordinated handling of data, and the patient's overall treatment, results in inefficiencies that can lead to increased total cost of care. In this regard, traditional fee-for-service healthcare models are far from ideal with respect to care quality and economics. The latter is evidenced by the untenable continued rise in healthcare costs in the United States under the fee-for-service model.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the present disclosure. The present disclosure may include the following various aspects and embodiments.

According to an exemplary embodiment of the present disclosure, a method for determining a patient's risk of developing an infection is disclosed. In one embodiment, the method comprises extracting patient data from one or more databases corresponding to a pool of patients receiving treatment; using one or more predictive models with the extracted patient data to generate, for each of the patients in the pool of patients, a respective patient risk score for developing an infection within a selected time period; generating a report including at least a portion of the identified subset of the pool of patients and their respective patient risk scores; and transmitting the report to one or more health care facilities, the one or more health care facilities further identifying one or more patients from the portion of the identified subset of the pool of patients for interventional treatment, consultation, training, or combinations thereof.

In this and other embodiments, the method further comprises wherein the one or more predictive models are arranged and configured to: analyze the extracted patient data to identify patient characteristics common to patients having previous documented reports of infections; and identify the patient characteristics in each of the patients in the pool of patients when generating the patient risk score for developing an infection within a selected time period.

In this and other embodiments, the method further comprises wherein the one or more predictive models are arranged and configured to: analyze the extracted patient data to identify patient characteristics common to patients who have not had previous documented reports of infections.

In this and other embodiments, the method further comprises wherein the one or more predictive models are arranged and configured to: identify characteristics of patients previously diagnosed with an infection; and analyze the extract patient data against the characteristics for commonalities.

In this and other embodiments, the method further comprises wherein the interventional treatment, consultation, or training comprises: transmitting to one or more patients a questionnaire to obtain additional information about the patient's administration of dialysis; contacting one or more patients to determine appropriate interventions to aid in minimizing a risk of developing the infection; contacting one or more patients for an assessment of a patient's dialysis treatment; altering one or more conditions regarding the patient's administration of dialysis; or sending a medical profession to one or more patients from the portion of the identified subset of the pool of patients for an in-home visual assessment; or combinations thereof.

In this and other embodiments, the method further comprises wherein the report is generated on a predetermined periodical basis.

In this and other embodiments, the method further comprises wherein the identified subset of the pool of patients comprises patients in a similar geographic area, patients assigned to a dialysis clinic, or a group of patients receiving care from an individual medical professional, or combinations thereof.

In this and other embodiments, the method further comprises wherein the report comprises a subset of the pool of patients having a respective patient risk score that is higher than a predetermined threshold value.

In this and other embodiments, the method further comprises wherein the predetermined threshold value is determined by the one or more predictive models based on historical data.

In this and other embodiments, the method further comprises wherein the report includes all patients associated with a particular medical group.

In this and other embodiments, the method further comprises wherein the report includes one or more associated reasons for each patient.

In this and other embodiments, the method further comprises wherein the extracted patient data comprises patient demographics, laboratory values, recorded information, physician notes, or treatment data, or combinations thereof.

In this and other embodiments, the method further comprises wherein the patient demographics comprises gender, race, age, or marital status, or combinations thereof.

In this and other embodiments, the method further comprises wherein the laboratory values comprise a patient's albumin level, a patient's calcium level, a patient's chloride level, a patient's creatinine level, or a patient's transferrin saturation (TSAT) level, or combinations thereof.

In this and other embodiments, the method further comprises wherein the laboratory values comprise a time period over which a patient has been undergoing dialysis treatments, a time period over which a patient was last diagnosed with an infection, a total number of previous infections from a patient, or a distance of a patient's home to a dialysis facility, or combinations thereof.

According to an exemplary embodiment of the present disclosure, a system for determining a patient's risk of developing an infection is disclosed. In one embodiment, the system comprises: an integrated care system configured to: extract patient data from one or more databases corresponding to a pool of patients receiving treatment; use one or more predictive models with the extracted patient data to generate, for each of the patients in the pool of patients, a respective patient risk score for developing an infection within a selected time period; generate a report including at least a portion of the identified subset of the pool of patients and their respective patient risk scores; and transmit the report to one or more health care facilities, the one or more health care facilities further identifying one or more patients from the portion of the identified subset of the pool of patients for interventional treatment, consultation, training, or combinations thereof.

In this and other embodiments, the system comprises wherein the one or more predictive models are arranged and configured to: analyze the extracted patient data to identify patient characteristics common to patients having previous documented reports of infections; and identify the patient characteristics in each of the patients in the pool of patients when generating the patient risk score for developing an infection within a selected time period.

In this and other embodiments, the system comprises wherein the one or more predictive models are arranged and configured to: analyze the extracted patient data to identify patient characteristics common to patients who have not had previous documented reports of infections.

In this and other embodiments, the system comprises wherein the one or more predictive models are arranged and configured to: identify characteristics of patients previously diagnosed with an infection; and analyze the extract patient data against the characteristics for commonalities.

In this and other embodiments, the system comprises wherein the interventional treatment, consultation, or training comprises: transmitting to one or more patients a questionnaire to obtain additional information about the patient's administration of dialysis; contacting one or more patients to determine appropriate interventions to aid in minimizing a risk of developing the infection; contacting one or more patients for an assessment of a patient's dialysis treatment; altering one or more conditions regarding the patient's administration of dialysis; or sending a medical profession to one or more patients from the portion of the identified subset of the pool of patients for an in-home visual assessment; or combinations thereof.

In this and other embodiments, the system comprises wherein the report is generated on a predetermined periodical basis.

In this and other embodiments, the system comprises wherein the identified subset of the pool of patients comprises patients in a similar geographic area, patients assigned to a dialysis clinic, or a group of patients receiving care from an individual medical professional, or combinations thereof.

In this and other embodiments, the system comprises wherein the report comprises a subset of the pool of patients having a respective patient risk score that is higher than a predetermined threshold value.

In this and other embodiments, the system comprises wherein the predetermined threshold value is determined by the one or more predictive models based on historical data.

In this and other embodiments, the system comprises wherein the report includes all patients associated with a particular medical group.

In this and other embodiments, the system comprises wherein the report includes one or more associated reasons for each patient.

In this and other embodiments, the system comprises wherein the extracted patient data comprises patient demographics, laboratory values, recorded information, physician notes, or treatment data, or combinations thereof.

In this and other embodiments, the system comprises wherein the patient demographics comprises gender, race, age, or marital status, or combinations thereof.

In this and other embodiments, the system comprises wherein the laboratory values comprise a patient's albumin level, a patient's calcium level, a patient's chloride level, a patient's creatinine level, or a patient's transferrin saturation (TSAT) level, or combinations thereof.

In this and other embodiments, the system comprises wherein the laboratory values comprise a time period over which a patient has been undergoing dialysis treatments, a time period over which a patient was last diagnosed with an infection, a total number of previous infections from a patient, or a distance of a patient's home to a dialysis facility, or combinations thereof. Further features and aspects are described in additional detail below with reference to the appended Figures.

BRIEF DESCRIPTION OF THE DRAWINGS

By way of example, embodiments of the disclosed methods and devices will now be described, with reference to the accompanying drawings, in which:

FIG. 1B is a flowchart illustrating an exemplary embodiment of a process for determining and treating for a risk of infection in dialysis patient in accordance with the present disclosure;

FIG. 1C is an exemplary embodiment of a charting of patient data for determining and treating for a risk of infection in dialysis patients in accordance with the present disclosure;

FIG. 14 is a diagram illustrating another exemplary embodiment of a dialysis system in accordance with the present disclosure.

DETAILED DESCRIPTION

Figure 1A:
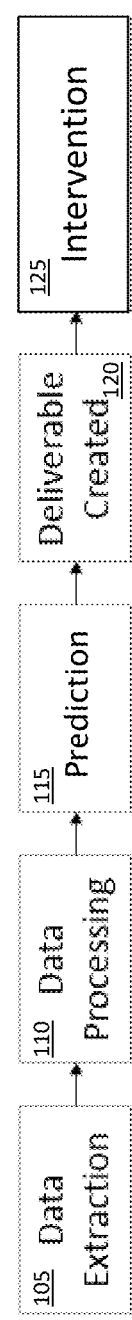
FIG. 1A is a flowchart illustrating an exemplary embodiment of a method for determining and treating for a risk of infection in dialysis patients in accordance with the present disclosure.

The present embodiments will now be described more fully hereinafter with reference to the accompanying drawings, in which several exemplary embodiments are shown. The subject matter of the present disclosure, however, may be embodied in many different forms and types of methods and devices for dialysis machines and other potential medical devices, diagnostics, and treatments for various diseases, and should not be construed as limited to the embodiments set forth herein. Rather, these embodiments are provided so that this disclosure will be thorough and complete, and willfully convey the scope of the subject matter to those skilled in the art. In the drawings, like numbers refer to like elements throughout.

Example embodiments described herein are suitable for implementing value-based care, which is an alternative to the fee-for-service healthcare model. Under a value-based healthcare system (also known as a "pay for performance" model), healthcare providers are provided with financial incentives tied to quality and efficiency of care and patient outcomes.

Some example embodiments are configured to provide coordinated care to a population of patients with a chronic disease, such as chronic kidney disease (CKD). CKD is a progressive disease marked by reduced kidney function. Once the kidney function drops below a threshold, the patient is considered to have kidney failure, or end-stage renal disease (ESRD). ESRD is the final stage of CKD and requires dialysis treatments for the remainder of the patient's life (absent a transplant).

In the United States, one model of value-based care in which example embodiments described herein may be implemented is the Comprehensive ESRD Care (CEC) Model, which is a type of accountable care organization (ACO) model developed under the authority of the U.S. Center for Medicare and Medicaid Innovation. In order to implement the CEC model, ESRD Seamless Care Organizations (ESCOs) are formed. An ESCO is an ACO that is formed by healthcare suppliers and providers voluntarily coming together. The resulting ESCO is a legal entity that provides coordinated care to ESRD beneficiaries through the CEC model.

Under the ESCO model, the ESCO shares savings and losses incurred by the U.S. Centers for Medicare and Medicaid Services (CMS) for the ESCO's beneficiaries. Savings or losses are determined by CMS based on an expenditure benchmark, which is derived from a baseline that reflects historical expenditure data for like or similar beneficiaries. The benchmark is compared to the actual Medicare Fee-For-Service (FFS) Part A and B expenditures for the aligned patient population in a performance year. The savings are also subject to an adjustment based on quality performance. Any reduction in costs directly translates to increased shared savings (profits), since the costs are measured against the predetermined benchmark. Quality of care is incentivized by the quality performance adjustment to the calculated shared savings.

The ESCO is responsible for each patient's overall care, which goes beyond dialysis treatments. For example, if a patient is admitted to the hospital for any reason (for example, infections, vascular dialysis access complications, and/or cardiac complications), the cost of the hospitalization counts against the yearly savings calculation. Since hospital admissions are especially costly, it is highly advantageous for ESCOs to keep the patients out of the hospital from a financial perspective. Example embodiments described herein implement a holistic approach to oversee and manage all aspects of the patients' well-being, which improves the quality of care while increasing efficiency of medical resources and overall cost efficiency.

Some example embodiments described herein analyze medical data of the applicable patient population in order to target high-risk patients with interventions to reduce the likelihood of hospitalization. Some examples analyze patient data to predict when a patient is likely to experience a particular health-related event or stage of disease progression and provide/adjust treatment accordingly.

In accordance with example embodiments, patient information may be sent to, managed within, and/or be accessible by, a coordinated care system, so that patients may receive high quality, efficient, coordinated health-care within a managed system that is able to intelligently manage and coordinate the patient's overall care. Incorporation of a coordinated care system may allow for better control of health care costs, e.g., by providing value-based care to patients in place of fee-for-service care. For example, as mentioned above, the population of patients diagnosed with ESRD has been increasing over time, often caused by several other diseases, including but not limited to diabetes, hypertension, and/or glomerulonephritis. Patients living with ESRD may face additional challenges due to the nature of the disease. For example, required lifestyle changes may lead to mental health deterioration. Additionally, at-home treatments may lead to increased isolation from medical professionals. As the healthcare landscape changes, opportunities to provide patients with resources for coordinating treatment may deliver additional patient health benefits beyond dialysis treatment.

Although exemplary embodiments described herein are related to renal diseases, it is understood that coordinated care systems and infrastructures described herein may be applicable to other chronic illnesses as an alternative or in addition to renal disease. Such other conditions may include, as non-limiting examples, cardiovascular related illnesses, pulmonary, gastrointestinal, neurological, urological, or gynecological conditions, diabetes, circulatory diseases, Alzheimer's or other dementias, asthma, COPD, emphysema, cancer, obesity, tobacco use, cystic fibrosis, or combinations thereof. Moreover, although some examples are described with respect to implementations in renal-related ACOs, such as ESCOs, it should be understood that the examples described herein may be analogously implemented in other ACOs with respect to other diseases or patient populations, and/or any other suitable value-based healthcare models.

Patients with CKD and/or ESRD are undergoing long-term care for kidney disease, e.g., by dialysis treatments. For example, some patients may receive dialysis treatments by peritoneal dialysis (see also FIGS. 13A-13B). As described below, a patient may need to exchange one or more dialysate bags during a peritoneal dialysis treatment, during which time a catheter for accessing the patient's peritoneum may become contaminated and lead to infection such as peritonitis. Peritonitis, an inflammation of the peritoneum typically caused by a bacterial or fungal infection, may result in a patient having to modify the current peritoneal dialysis treatment, be retrained in the methodology for the peritoneal dialysis treatment, or switch dialysis modalities, e.g., the patient is no longer a candidate for peritoneal dialysis. A patient may be switched to a hemodialysis procedure (see FIG. 14), which is typically administered in a clinical setting. For less ambulatory patients, patients living in rural areas, and/or patients suffering from other conditions, maintaining regular dialysis appointments at a clinic facility may be difficult to coordinate such that the patients may miss receiving critical dialysis treatments.

In accordance with exemplary embodiments of the present disclosure, a care framework may be configured to identify and treat patients at risk for infection, e.g., peritonitis. A significant patient volume of data may provide information to the systems such that a machine learning model may be trained to determine patient characteristics from documented reports of peritonitis, as well as historical patient data having no identified infection diagnosis, for identifying patients at risk for developing peritonitis over a future selected time period, so that interventional treatment and/or training may be provided to the patient to minimize risk of infection, or reduce the volume, severity and/or frequency of future infections. By minimizing or avoiding infections, patients may continue receiving peritoneal dialysis treatments in a home environment, minimizing potential missed treatments, among other advantages. It is also understood that systems and methods in accordance with the present disclosure may be utilized to provide a similar methodology for identifying and/or treating a patient risk of infection from a treatment other than dialysis.

For example, in various embodiments, the care framework may compare historical patient data where infections developed within a selected time period to a patient's data. The care framework may further evaluate the patient data for the respective infection risk and/or identify the patient data having the infection risk. The care framework may further generate interventional medical treatment to the patient based on the identified infection risk. In various embodiments, the risk of developing an infection includes the patient receiving dialysis treatment in a first modality of peritoneal dialysis. The interventional treatments may include retraining the patient regarding the first modality of peritoneal dialysis, modifying peritoneal dialysis treatment of the patient, and/or switching the patient from the first modality to a second modality of hemodialysis. Other interventions may include altering how, and/or under what conditions, the patient administers the peritoneal dialysis treatment. Examples of such altering may include: (a) modifying equipment set-up and/or administration of the peritoneal dialysis operation to comply with guidelines, (b) modifying equipment storage practice to comply with guidelines, (c) reducing or eliminating instances of handling the catheter without proper washing of hands, (d) increasing utilization of contamination prevention supplies such as gloves and face masks, and (e) removing or minimizing environment sources of equipment contamination. Such interventions may be implemented, for example, by educating/guiding the patient (and/or other individual(s) that may be involved with the treatment or the environment in which the treatment occurs) and/or providing suitable equipment and/or supplies.

In embodiments, patient demographics, data (e.g., lab test results) and recorded information (e.g., treatment notes) for patients receiving dialysis treatments may be analyzed by one or more programs and/or algorithms for determining a risk of the patient for developing an infection during a future time period. In some embodiments, risk levels may be evaluated for a likelihood of developing an infection within one month. In other embodiments, the time period may be less than one month, and/or greater than one month. The care framework may be configured to perform a method of determining a patient risk for developing an infection (e.g., peritonitis) to generate a report by analyzing the selected patients for a risk level. FIG. 1A, for example, illustrates a flowchart of an exemplary method 100 for determining a patient risk of developing an infection. At step 105, data may be extracted. Data from the selected patients may be extracted by the integrated care system, or a care analysis and guidance system, from other clinical systems, outside systems, and/or other databases as illustrated in FIGS. 6-11.

As described above, numerous variables may be utilized by the integrated care system, at step 105 of FIG. 1A, including patient demographics, laboratory values, treatment data and comprehensive assessments. For example, FIG. 1B illustrates an exemplary embodiment of a chart 130 of variables 135a, 135b, . . . 135n, which may be included for determining a patient risk of developing an infection (e.g., peritonitis). It is understood that any number "n" of variables may be utilized for determining patient risk. Patient demographics may include gender and race, as well as age, marital status, and the like. Laboratory values may be patient data such as albumin, calcium, chloride, creatinine, transferrin saturation (TSAT), and the like. Additionally, laboratory data may be calculated in various manners, e.g., providing an average over a specified time period, a maximum value, a minimum value, a value spike and/or dip, standard deviation, and trending values, for analysis by the integrated care system. Additional variables may also be included, such as a time period a patient has been receiving or self-administering at-home dialysis treatments (e.g., a total number of days), a time period a patient was last diagnosed with an infection (e.g., a total number of days), a total number of previous infections from a patient, and/or a distance of a patient's home to a dialysis facility. In some embodiments, patient data elements used in this predictive model may be sourced from a data warehouse, knowledge center, and/or central data repository, which may be periodically updated (e.g., daily) with new patient information from one or more medical record data collection systems used by dialysis patient care staff (e.g. nurses, physicians, dieticians, social workers and the like). The data warehouse may also include other patient parameters such as lifestyle and other community-level psychosocial metrics from a third-party vendor which are matched to patients. For example, community-level metrics may be matched to patients based on geographic location, e.g., as defined by the associated zip code.

It is understood that raw data variables may be transformed through feature engineering to create additional variables and/or features, based on analysis of data patterns, and clinical experience. Data may include patient vitals, e.g., blood pressure, weight, pulse, temperature, respiration rate, and like. Data may also be calculated in various manners, e.g., providing an average over a specified time period, a maximum value, a minimum value, a value spike and/or dip, and trending valves, for analysis by the integrated care system. Similar to laboratory values, raw data variables of data may be transformed through feature engineering to create additional variables and/or features, based on analysis of data patterns, and clinical experience.

Referring back to FIG. 1A, at step 110, extracted patient data as described for example with respect to FIG. 1B at step 105, may be processed by the integrated care system. The patient data for processing may be measured data, calculated data, written notes, and the like. Some of the extracted data (e.g., measured data, calculated data) may be numerical, and some (e.g., clinician notes) may be text and/or graphics.

In some examples, at processing step 110, some or all of the patient data that is in the form of numerical data may be processed to be in a more suitable form for further analysis by the integrated care system. This processing may include, for example, scaling and conversion. In some examples, this processing may include screening to ensure that the data is within a feasible range in order to filter out or identify erroneous data. In some examples, some or all of the extracted numerical data remains in its original, unmodified form through processing step 110.

In accordance with some examples, also at 110, graphical extracted data (e.g., handwritten clinician notes) is converted to text data prior to further analysis. In some examples, this is accomplished by applying word2vec and/or a convolutional neural network, although other suitable algorithms may be utilized in place of, or in addition to, these. Word2vec algorithms may include CBOW (continuous bag of words) and/or distributed representation of words.

The text data, including any text recognized from graphics as described above, is analyzed for the presence of words, phrases, and/or word proximities that indicate particular clinician-observed conditions and/or events corresponding to the patient and/or treatment. In some examples, the conditions and events are identified by the integrated care system from among a group of conditions and events stored in a database. When such conditions and events are correlated via the analysis of the text, the integrated care system creates or modifies one or more numeric identifiers to reflect the conditions and events. In some examples, where the text identifying the condition indicates a magnitude or degree of severity (e.g., "pain level 7.5/10," or "high," "low," etc.) the integrated care system may generate or modify the numeric identifier such that it reflects the magnitude or severity. The numeric identifiers allow the presence and/or magnitude of the condition or conditions to be further analyzed by the integrated care system.

In some embodiments, as illustrated at step 115 in the illustrated example of FIG. 1A, the processed data (including any of the numeric identifiers corresponding to text data) may be sent to one or more algorithms of the integrated care system for analysis and prediction. As described above, historical patient data may be utilized by the integrated care system for training a machine learning model for analysis of current patient data for identifying a risk of future infections.

One or more algorithms may analyze selected patient data for determining a risk of a patient developing an infection such as peritonitis within a selected time period (e.g., one month), e.g., at step 115. As described above, patient data described in FIG. 1B may be utilized by the integrated care system to determine a risk score that each selected patient may develop an infection within the next month. In some examples, the algorithm (e.g., the gradient boosting framework and/or extreme gradient boosting tree algorithm) may analyze the specific patient's data in the context of the corresponding data of a pool of other patients.

In some examples, the analysis/prediction algorithm of the integrated care system examines and analyzes an entire pool of patients in order to assign for each patient a respective risk score for developing an infection within a preselected time period. It should be understood, however, that in some examples, the algorithm may be run for a single patient or any suitable number of selected patients from the pool.

At step 120, a document may be generated by care framework, which may be utilized by a care navigation unit 230. Referring now to FIG. 1C, a report 140 may be generated by the integrated care system of a selected group of patients, and identifying those having a risk of developing an infection within a selected time period. The report 140 may be generated by the integrated care system by periodically running the selected patient data against the trained machine learning model (e.g., a report 140 may be generated monthly, for identifying patients at-risk for developing peritonitis within the next month). In some embodiments, the selected group of patients may be patients in a similar geographic area, assigned to a dialysis clinic for treatment, a group of patients receiving care from an individual medical professional, and/or other grouping. In some embodiments, a report 140 may indicate a patient (e.g., name, medical record number, or other identifying characteristic such as a social security number or the like), a risk score associated with developing an infection (e.g., peritonitis) over a selected time period (e.g., within one month), and the associated reasons for each patient. For example, patient John Smith may be determined by the integrated care system to be at risk developing an infection, having a calculated risk score of approximately 82.67%. Associated reasons identified by the integrated care system may include abnormal lab values (e.g., John Smith's albumin, chloride, and TSAT levels are identified as being outside acceptable ranges), and that the patient last had a previous infection 45 days before the report was generated. It is understood that the reasons associated with John Smith's risk score determination may include a medical professional's written notes of patient care, and/or the integrated care system may have calculated one or more parameters based on measured patient vitals, e.g., at the dialysis treatment (e.g., albumin, chloride, TSAT, etc.). The report 140 may further include additional patients, e.g., Jane Doe, who may also be identified as being at-risk for developing an infection within a future time period. For example, Jane Doe may have a calculated risk score of 81.75% of developing an infection (e.g., peritonitis) within a selected time period (e.g., within one month), based on lab values such as creatinine, calcium, and chloride levels, as well as a previous infection 37 days before the report was generated.

Figure 1D:
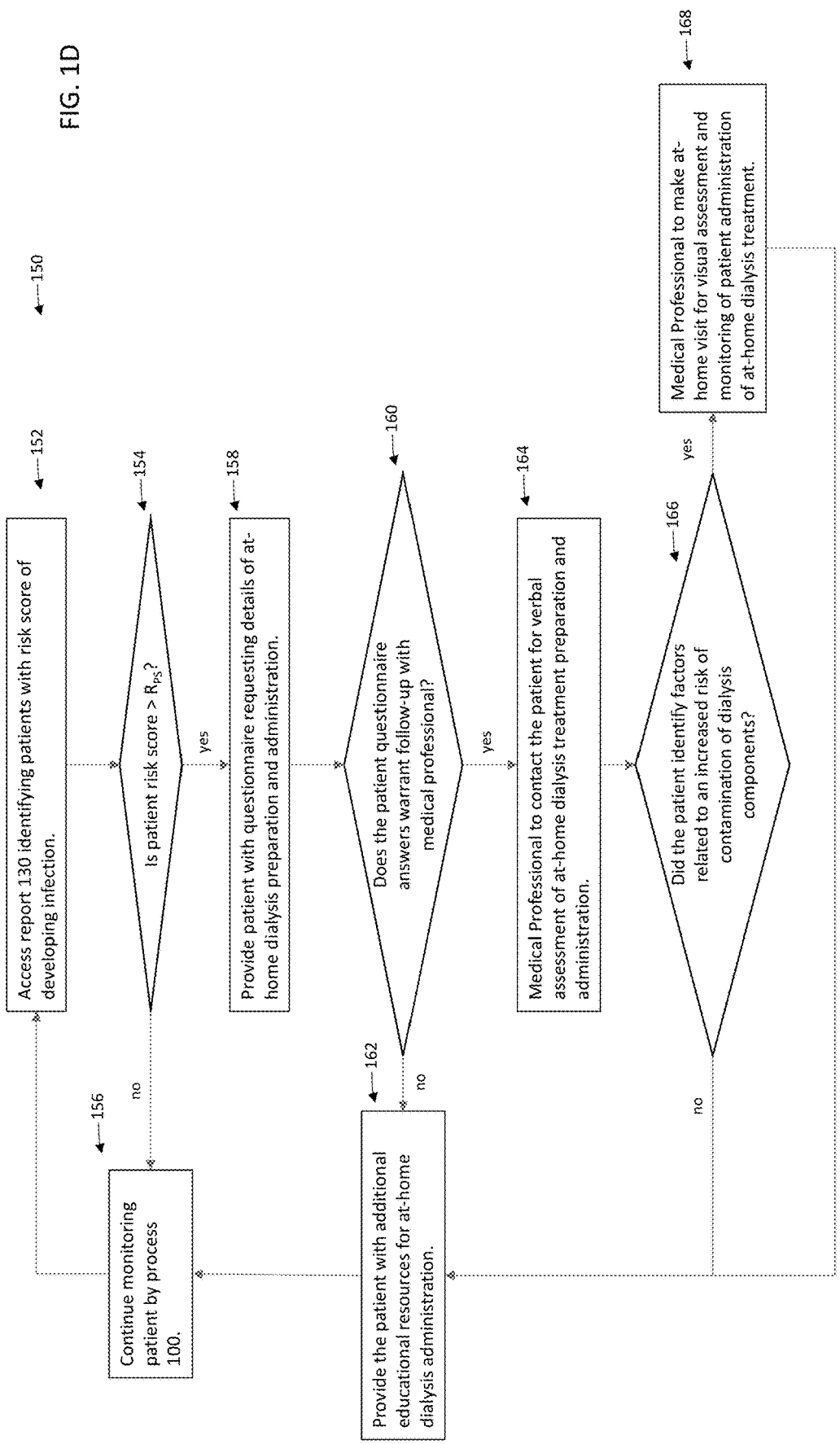
FIG. 1D is a flowchart illustrating an exemplary embodiment of a process for determining and treating for a risk of infection in dialysis patients in accordance with the present disclosure.

In embodiments, the report 140 may be generated so that patients are ranked according to their associated calculated probabilities. This report 140 may be provided to the care coordination unit 125 (e.g., care navigation unit) so that medical professionals may assess patient parameters and recommend treatment interventions. Referring back to FIG. 1A, at step 125, the report 140 may be utilized in intervention and patient treatment. Equipment (e.g., catheter) contamination is one factor leading to an infection of a patient, as the patient inserts the catheter into the abdomen for peritoneal dialysis treatments. Additionally, since peritoneal dialysis procedures are typically performed in a home environment, patients may not be supervised and/or may unintentionally expose equipment to contamination. Referring now to FIG. 1D, a flowchart 150 illustrating an exemplary embodiment of a process of the care framework 200 for handling the report 140 and interventional patient treatment to minimize a risk of the patient developing an infection, such as peritonitis, is shown.

Identified patients on the report 140 may be subject to additional consultation and interventional treatments at step 152. In some embodiments, the report 140 may identify only patients deemed to be at-risk for developing an infection within the next month. In some embodiments, the report 140 may identify an entire selected patient population, such as all patients associated with a medical professional (e.g., primary care physician), and/or associated with a selected geographic area. At step 154, if the patient risk score is greater than a predetermined threshold "$R_{PS}$", the patient may be identified for further assessment by a medical professional. In some embodiments, the predetermined threshold $R_{PS}$ may be any identified risk score level at which a patient is deemed at risk. For example, an analysis of the patient population may determine the predetermined threshold $R_{PS}$. In some embodiments, the predetermined threshold may be determined by the analysis to be 50%. In some embodiments, the predetermined threshold may be determined by the analysis to be any risk score between approximately 50% and 80%. If the patient risk score is less than the predetermined threshold, the patient may continue to be monitored at step 156, e.g., the integrated care system, or care analysis and guidance system, may continue to run the patient data against the machine learning model for the following month's assessment.

A patient identified as being at risk for developing an infection at step 154 may initially receive a questionnaire or other type of survey for additional information related to their preparation for and administration of at-home peritoneal dialysis at step 158, which may be directed to a medical professional for assessment and/or included in the integrated care system 220. The questionnaire may include general questions for the patient regarding their preparation and administration of at-home dialysis. For example, the patient may be storing dialysis supplies and/or equipment in an area accessible by a pet, which may lead to contamination. In some embodiments, the patient may be forgetting or not thoroughly washing hands before handling dialysis supplies, or the patient may not be donning safety protection such as gloves and/or a mask, to minimize risk of contamination, which may be quickly determined through the patient questionnaire. If the patient is properly preparing and administering dialysis at home and adhering to instructions to minimize contamination, additional follow-up by a medical professional may not be warranted (see step 160), and at step 162, the patient may be provided with additional educational resources for staying infection-free.

In some embodiments, based on the questionnaire, the patient may be identified at step 160 as benefitting from additional intervention by a medical professional. At step 164, a nurse, clinician, or other medical professional may contact the identified patients to determine appropriate interventions to aid in minimizing or eliminating the risk of developing or perpetuating an infection. In some embodiments, the medical professional may contact the patient for an assessment of the dialysis treatment, such as a telephone call, to discuss a patient's at-home dialysis procedure. The medical professional may be able to assess verbally if the patient is adhering to recommended storage guidelines of equipment, hand washing policies prior to handling of the catheter, and/or other standard procedures for minimizing a risk of catheter contamination. The medical professional may also be able to verify if a patient has the proper equipment and contamination prevention supplies such as gloves and/or face masks, whether the patient has one or more pets that may be contributing to potential equipment contamination, and/or if another household member or caregiver may be unintentionally contributing to equipment contamination.

At step 166, the medical professional may assess whether additional factors identified by the patient may be related to an increased risk of developing an infection. For example, the patient may have indicated a confusion related to the set-up and/or administration of the dialysis operation, and/or the patient may have indicated a complicated home environment, which may increase their risk of developing an infection through contamination of equipment. As described above, patients suffering from kidney disease may be less ambulatory and may not have full mobility to maintain a level of cleanliness needed in their homes, for proper preparation and administration of dialysis.

If additional factors are not identified at step 166, the patient may be provided with additional educational resources highlighting best practices and/or standardized instructions for preparation and administration of dialysis at home at step 162. The patient may then continue to be monitored on a monthly basis for future risk of developing an infection.

If the verbal assessment with the patient indicates additional factors leading to an increased risk of contamination, a medical professional may be sent to the patient's home for a home visit and visual assessment at step 168. In some embodiments, a medical professional may be sent to the patient's home to identify and potentially ameliorate areas of concern for sources of infection such as contamination. For example, a home nurse may visually observe a patient's preparation and administration of peritoneal dialysis, and identify areas for improvement, to reduce a risk of contamination of components. A patient having a history of infections may be more susceptible to future infections. As such, the patient continuing with peritoneal dialysis as a dialysis treatment modality may necessitate a higher standard of cleanliness in an effort to reduce potential contamination.

In some embodiments, upon a visual assessment of the patient's self-administration of peritoneal dialysis at step 168, the medical professional may determine that the patient may remain on peritoneal dialysis with retraining. For example, the patient may benefit from additional reminders of standard procedures to avoid contamination of components and thereby minimize risk of developing peritonitis. In some embodiments, the visual assessment may lead to a medical professional assessing that the risk of developing an infection is so great that that the patient may no longer benefit from this type of dialysis modality (e.g., at-home peritoneal dialysis). The medical professional may switch the patient from at-home peritoneal dialysis to hemodialysis, either administered at home and/or at a clinic setting, to further minimize and/or avoid developing an infection such as peritonitis.

In embodiments, the visual assessment may allow more patients to remain on peritoneal dialysis treatments for an extended period of time, by managing risk for developing peritonitis. As described above, patients may be less inclined to attend clinic appointments to receive hemodialysis, due to transportation concerns, mobility concerns, and/or other medical conditions and/or difficulties. However, missing dialysis appointments may lead to additional complications and/or developing other medical conditions related to kidney disease. As such, it may be advantageous to maintain patients on peritoneal dialysis as long as the patient is not subjected to unnecessary risk for developing peritonitis, in accordance with the present disclosure. It is also understood that peritoneal dialysis as a modality for administering dialysis treatments may be advantageous over other modalities for additional medical reasons.

Figure 2A:
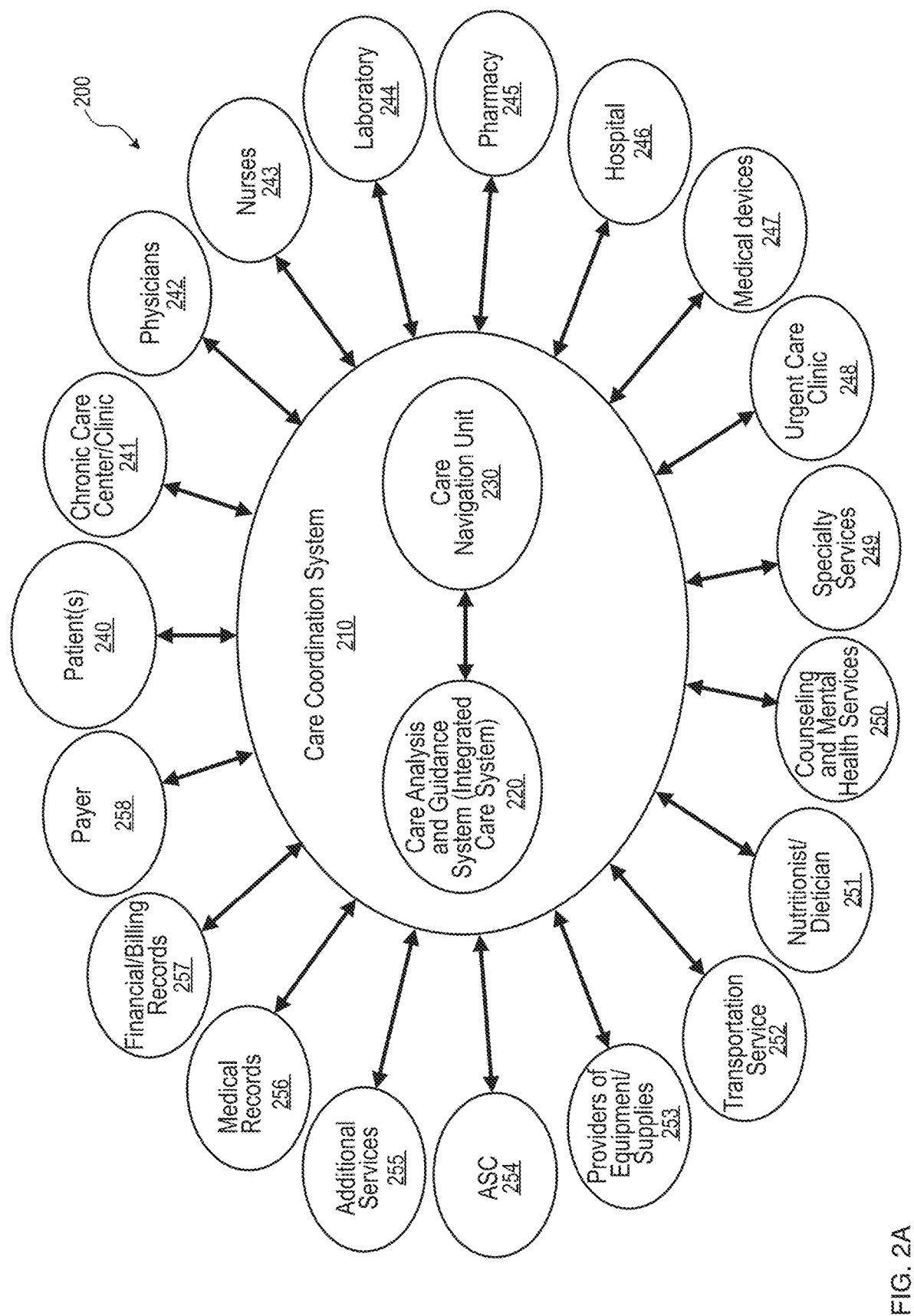
FIG. 2A is a diagram illustrating an exemplary embodiment of a system for providing coordinated healthcare in accordance with the present disclosure.

Referring to FIG. 2A, an example in accordance with the present disclosure includes a coordinated care framework 200 for treating a patient or population of patients 240. The overall care of the patient/population 240 is overseen and coordinated by a care coordination system 210. The care coordination system 210 includes a care analysis and guidance system 220 (which is referred to herein interchangeably as an "integrated care system"), which receives, analyzes, and creates data used to coordinate the care of the patient/population 240. The care coordination system 210 utilizes a care navigation unit (CNU) 230, which implements the coordinated care in accordance with data received from the care analysis and guidance system 220. To manage the overall health and well-being of the patient/population 240, the care coordination system 210 communicates with numerous relevant entities and components. In FIG. 2A, the double-arrow lines graphically represent communication and interaction flows/channels.

In the example illustrated in FIG. 2A, the care coordination system 210 coordinates care for the patients 240 among entities that include chronic care centers or clinics 241, physicians 242 (which may include nephrologists, especially for renal patients), nurses 243, laboratories 244 (e.g., blood labs or other diagnostic labs), pharmacies 245, hospitals 246, medical devices 247 (e.g., dialysis machines or other medical treatment/monitoring devices), urgent care clinics 248, specialty services 249, counseling and mental health services 250, nutritionists/dieticians 251, transportation services 252, providers of medical equipment and supplies 253, ambulatory surgical centers (ASCs) 254, additional services 255, medical records 256, financial and billing records 257, and payer(s) 258 (e.g., CMS or private insurer).

It should be understood that some example embodiments may include other entities not shown, and/or may exclude some of the entities shown. Further, it should be understood that the illustrated communication channels are not exclusive, and the various entities may also, where appropriate, communicate directly or indirectly between each other and/or the patients 240. In some examples, the communication between the care coordination system 210 and one or more of the other entities may be indirect, flowing through one or more intermediary entities. For example, coordination of nurses 243 may be conducted directly between the care coordination system 210 and the nurses 243 or via intermediary channels such as a clinic 241, 248, a hospital 246, or any other suitable channel.

In accordance with some examples, the framework 200 of FIG. 2A may be used in treating diseases such as the progression of kidney disease, e.g., End-Stage Renal Disease (ESRD) and/or Chronic Kidney Disease (CKD). Patients with ESRD are patients undergoing long-term care for kidney disease, e.g., by dialysis treatments. The care framework 200 may identify a risk score of a patient for a patient to develop an infection over a predetermined amount of time, e.g., peritonitis. Monitoring health status trends of dialysis patients may pose challenges. For example, patients may exhibit varying and irregular degrees of functional/cognitive impairment, and may be coupled with complex clinical abnormalities that are independent of a patient's length of time on dialysis. By identifying a risk score, a patient may receive interventional treatment, which may alter or reduce a risk of developing an infection. For example, proactively addressing potential concerns, a patient's risk of developing an infection may be decreased or even eliminated. In accordance with exemplary embodiments of the present disclosure, coordinated care framework 200, including care analysis and guidance system 220, may utilize one or more programs and/or algorithms for identifying a risk of infection in patients, and providing interventional treatment options to reduce and/or eliminate the risk of infection.

A care analysis and guidance system (integrated care system) 220 may include and execute various healthcare-related models and/or programs. In some examples, these models and/or programs are specifically adapted to implement or carry out particular value-based care frameworks (for example, ESCO models, other ACO models, Chronic Special Needs Plans (C-SNP's), and the like), whereas other examples may include models/programs generally applicable across multiple value-based care frameworks. It is also understood that additional types of value-based care models may be provided for other chronic illnesses, including but not limited to chronic kidney disease, or one or more of the other chronic diseases and conditions mentioned above. These healthcare models may influence improvements in providing value-based care to a patient, for example, by more efficiently managing a patient's care within a specified structure, and may replace conventional fee-for-service (FFS) models. Fee-for-service models may typically focus on volume over the quality of individualized patient care, with little incentive to improve a patient's overall health, which may be less efficient and have lower effectiveness than value-based models.

Shifting patient care away from conventional fee-for-service models to value-based healthcare models may improve care received by patients, reduce total costs, and may improve management of large patient populations diagnosed with the same chronic disease. For example, as mentioned above, value-based healthcare models may pay providers based on a quality of care (e.g., clinical outcomes, meeting specific performance criteria, etc.) received by the patients, and providers and patients may benefit from a focus on addressing and improving the overall health of patients. For example, CMS may set a budget for patient care for a diagnosed illness (e.g., ESRD), thereby incentivizing healthcare providers for innovations to lower costs in providing treatment to the illness. In some embodiments, payments may be associated, or negotiated through "shared risk" contracts, in which the cost, as well as savings, associated with an illness and the coordinated care of a patient is shared by the provider as well as the payer. This arrangement is present in the ESCO model described in greater detail above.

In some embodiments, a care coordination system may identify, test, and/or evaluate innovations through the CEC/ESCO framework for improving patient care to Medicare beneficiaries diagnosed with ESRD. The care coordination system may provide a structure for dialysis clinics, nephrologists or other specialists, and/or other providers to be connected to each other for care coordination for aligned beneficiaries. Value-based healthcare models may incentivize providers based on a quality of care of services delivered. For example, the care coordination system may incorporate incentives for improved care coordination, individualized patient care, and/or improved long-term health outcomes of a patient population. The care coordination system may also coordinate outcomes, e.g., clinical quality, financial, etc., measured by Medicare Part A (e.g., hospital insurance) and B (e.g., medical insurance) spending, including spending related to dialysis services for their aligned ESRD beneficiaries. It is understood that some value-based healthcare models may also include Medicare Part D (e.g., prescription drug coverage) spending.

An integrated care system 220 may form a part of a clinical system for diagnosing and treating a patient in all aspects of care. The integrated care system 220 may be connectable to additional clinical systems, including but not limited to a pharmacy, a CKD/ESRD data registry, and the like. For example, the integrated care system may automatically send prescriptions and other patient information to a pharmacy based on information provided by a medical professional, and may be able to send and receive data and information to the CKD/ESRD data registry, for comparison to other patients and projections for future treatment. The integrated care system may determine events associated with CKD/ESRD and take appropriate action, including but not limited to informing patients, informing clinicians of when specific interventions are warranted, and/or alerting clinicians to upcoming important dates for interventions.

One or more outside, or external, systems may also be connectable to the integrated care system 220. For example, the external systems may include one or more of diagnostic and/or treatment equipment such as a dialysis machine, labs, doctor's office, hospital, and/or electronic medical records. Patient information may be sent and received between the integrated care system and the external systems, so that patient care may be more efficient, standardized, and consistent across several functions. For example, the integrated care system 220 (see FIG. 2A) may receive information from a patient's electronic medical records, thereby accessing historical information. A dialysis unit, or dialysis machine, doctor's office, labs, and hospitals may send and receive information to and from the integrated care system based on patient treatment, diagnostics, or information beyond treatment or diagnostics.

As described below with respect to FIGS. 12-14, in some embodiments, a care coordination system may provide information to a dialysis machine 1200, 1300, 1400, for use in dialysis treatment. In some embodiments, the integrated care system may send the dialysis machine 1200, 1300, 1400, a prescription from a medical professional for a prescribed dialysis treatment, in which case the integrated care system may receive the prescription from a doctor's office or hospital. The integrated care system may also be able to verify the prescribed treatment against the patient's lab work or medical records, and in some instances may remotely program the prescription onto the patient's dialysis machine, or forward the prescription to the machine for local set-up. In this manner, the patient may be sure to receive the necessary and correct treatment and may be prevented from administering or receiving an improper amount of dialysis treatment, thereby reducing human error and improving patient care. The integrated care system 220 may also be able to inform the relevant medical professional based on information received from these external systems, as well as the additional clinical systems, e.g., to provide appropriate medical treatment to the patient and/or to indicate to a medical professional when patient retraining and/or additional supervision of treatment may be needed.

Figure 2B:
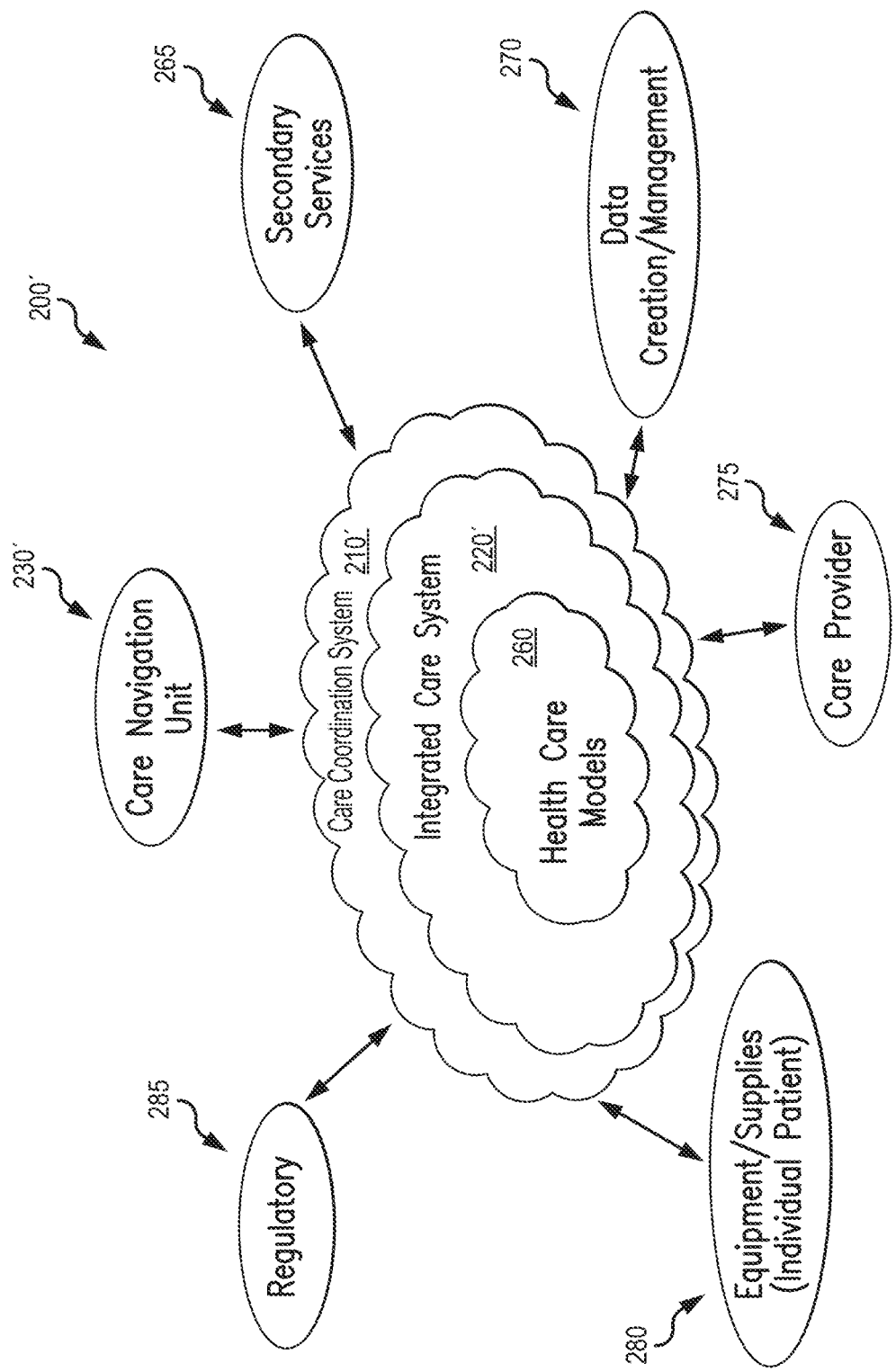
FIG. 2B is a diagram illustrating an exemplary embodiment of systems for assessing and treating disease, including kidney disease, in accordance with the present disclosure.

FIG. 2B is another illustration of a care coordination framework. Coordinated care framework 200' of FIG. 2B shares the features described herein with respect to coordinated care framework 200 of FIG. 2A except to the extent described otherwise. The coordinated care framework 200' described in this example is provided for integrating patient care in treating kidney disease, e.g., ESRD and/or CKD is shown (although it may be adapted as well for other chronic conditions similar to the framework of FIG. 2A). A care coordination system 210' may coordinate at least some aspects of a patient's care with the integrated care system 220' (which may include and execute healthcare-related models and/or programs 260), to support patient care. Various components may engage within the care coordination system 210' to provide complete patient care via the care framework. For example, any number of integrated care components may send and receive information to and from the integrated care system 220', including but not limited to a secondary services component 265, data creation and/or management component 270, care provider component 275, equipment and/or supplies component 280, and regulatory component 285. In some embodiments, the care coordination system 210' may engage with third party resources, including but not limited to lab services, research, etc. In some embodiments, the care framework may encompass, or is implemented by, or is associated with, a care navigation unit 230'. In the example of FIG. 2B, it is noted that the care navigation unit 230' is indicated as a separate entity from the care coordination system 210', but it should be understood that in other examples (see, e.g., FIG. 2A), the care navigation unit may be included as part of the care coordination system.

Figure 6:
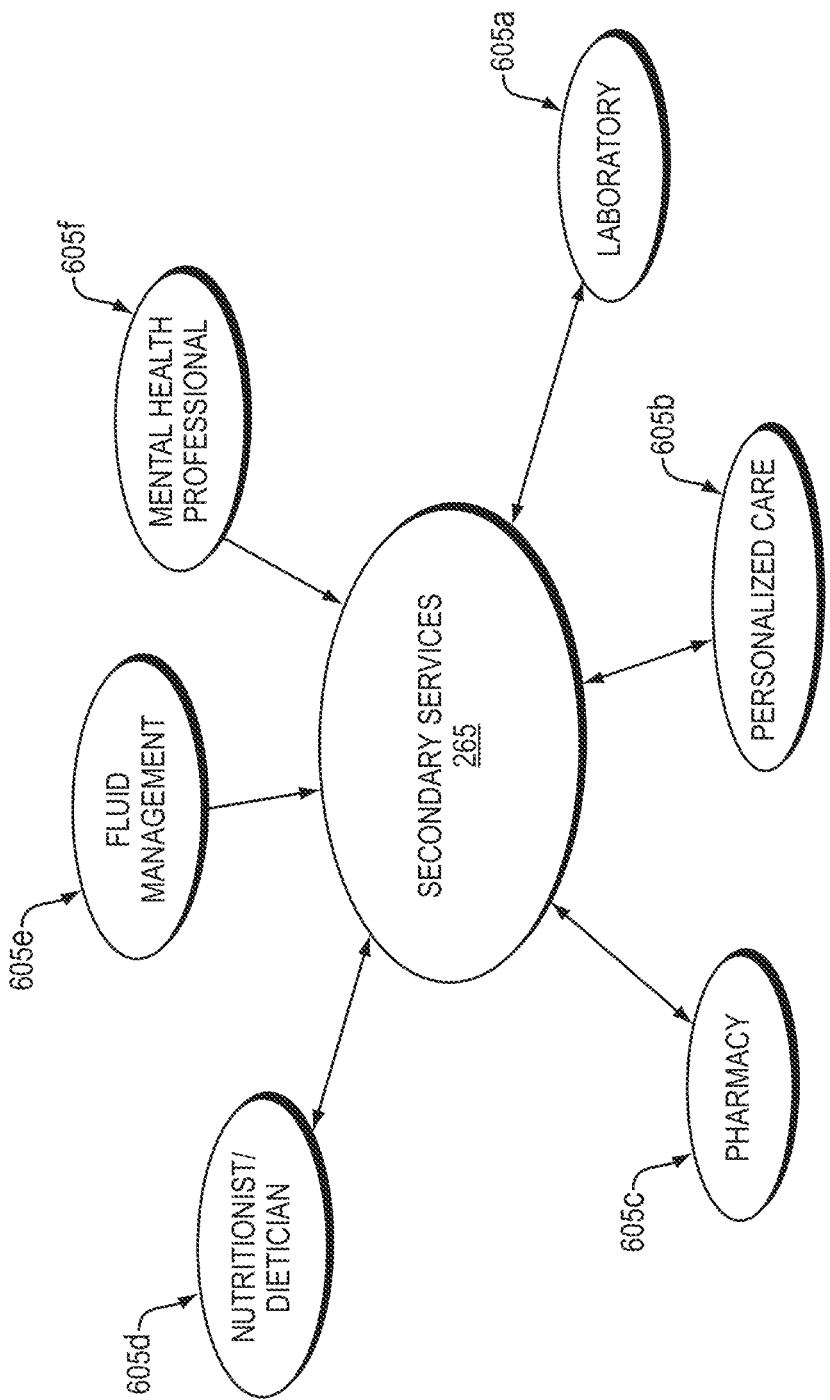
FIGS. 6-10 are diagrams illustrating exemplary embodiments of components of systems for providing coordinated healthcare, in accordance with the present disclosure.

Each component of an integrated care system (e.g., care analysis and guidance system) 220, 220' may include one or more units, including internal services and support as well as external services and support, as described above. As shown in FIG. 6, the secondary services component 265 may include any number "n" of services 605a, 605b, . . . 605n related to secondary patient services. For example, secondary services may include laboratory 605a, personalized care 605b, and/or pharmacy 605c. Each of the secondary services 605a, 605b, . . . 605n may send and receive patient information to the integrated care system 220, 220', for compilation and analysis. For example, a laboratory may automatically send results of patient bloodwork and other test results to the integrated care system 220, 220'. Additionally, the integrated care system 220, 220' may automatically send testing instructions to the laboratory for selected tests on patient samples, based on determinations from medical professionals, and/or other information gathered by the care coordination system 210' via a care framework. Similarly, the integrated care system 220, 220' may automatically send prescriptions and dosage instructions to a pharmacy based on a patient's test results and other factors determined by the integrated care system 220, 220'. The pharmacy may also send information to the integrated care system 220, 220' related to other patient prescriptions for potential adverse drug interactions, how timely a prescription is refilled, and/or patient interaction with the pharmacist, etc.

In some embodiments, a patient may benefit from care by a nutritionist and/or dietician 605d, to adjust to dietary restrictions as a component to their care. For example, ESRD patients may have prescribed dietary requirements as part of receiving hemodialysis and other treatment for their kidney disease. A patient may benefit from consultation with a nutritionist and/or dietician, for moving towards a healthier eating lifestyle and other potential health-related benefits. Fluid management 605e may also be managed for a patient, to ensure a patient is receiving proper amounts and types of fluid. Patients living with CKD and/or ESRD may have fluid restrictions for better dialysis outcomes. Some patients may have difficulty in understanding liquid intake, and/or may be unable to reliably track their fluid intake. In some embodiments, fluid management may be managed by a nutritionist and/or dietician, although it is understood that in other embodiments a patient's fluid intake may be managed by another medical professional. In embodiments, a patient may benefit from care by mental health professionals 605f, for example, psychologists, psychiatrists, and/or other counseling services. As described above, a patient's mental well-being may be affected by progression of an illness, and may otherwise be missed by other medical professionals in the course of treatment. As such, scheduling and providing access to mental health professionals may improve the patient's total health.

Figure 7:
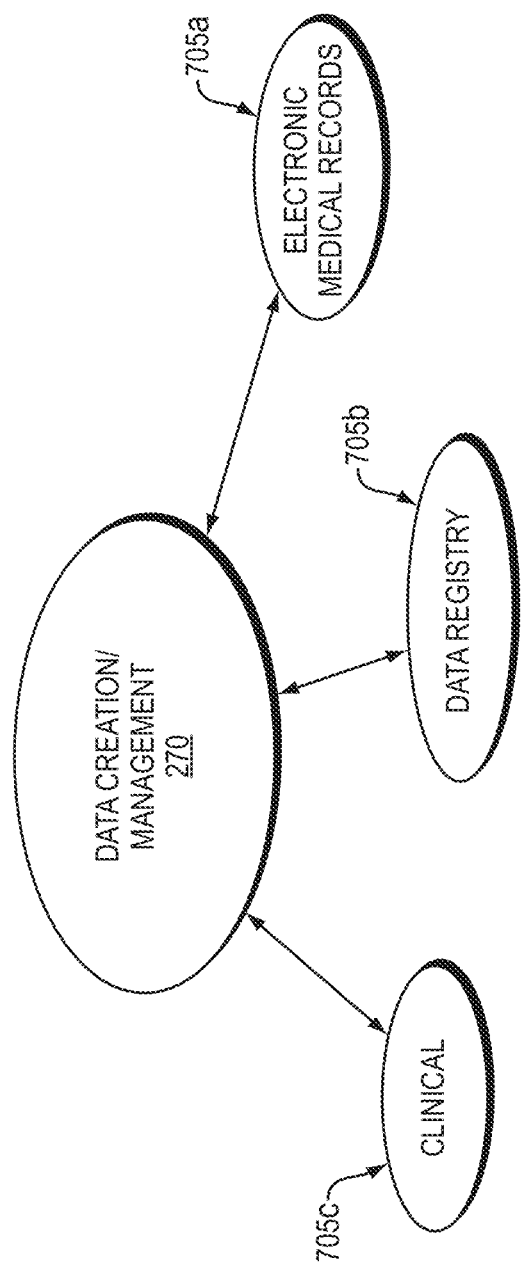

Referring now to FIG. 7, the data creation/management component 270 may include one or more units related to the creation and/or management of patient data, including internal services and support as well as external services and support, as described above. For example, the data creation/management component 270 may include any number "n" of services 705a, 705b, . . . 705n. As shown in FIG. 7, electronic medical records (EMR) 705a, data registry 705b, and clinical information 705c, may receive, store, and/or send patient data records as determined by the care analysis and guidance system 220, 220'. For example, a patient's medical records may be automatically updated after receiving lab results, treatment information, and/or notes from medical professionals. The care analysis and guidance system 220, 220' may utilize a patient's medical records for trends or triggering events, so that the care coordination system 210' may provide relevant information to a medical professional for treatment and other care option recommendations and timing and coordination of various types of possible interventions. In some embodiments, the care analysis and guidance system 220, 220' may analyze multiple patients as part of a data registry, for determining global trends and analyzing data from a macro-level.

Figure 8:
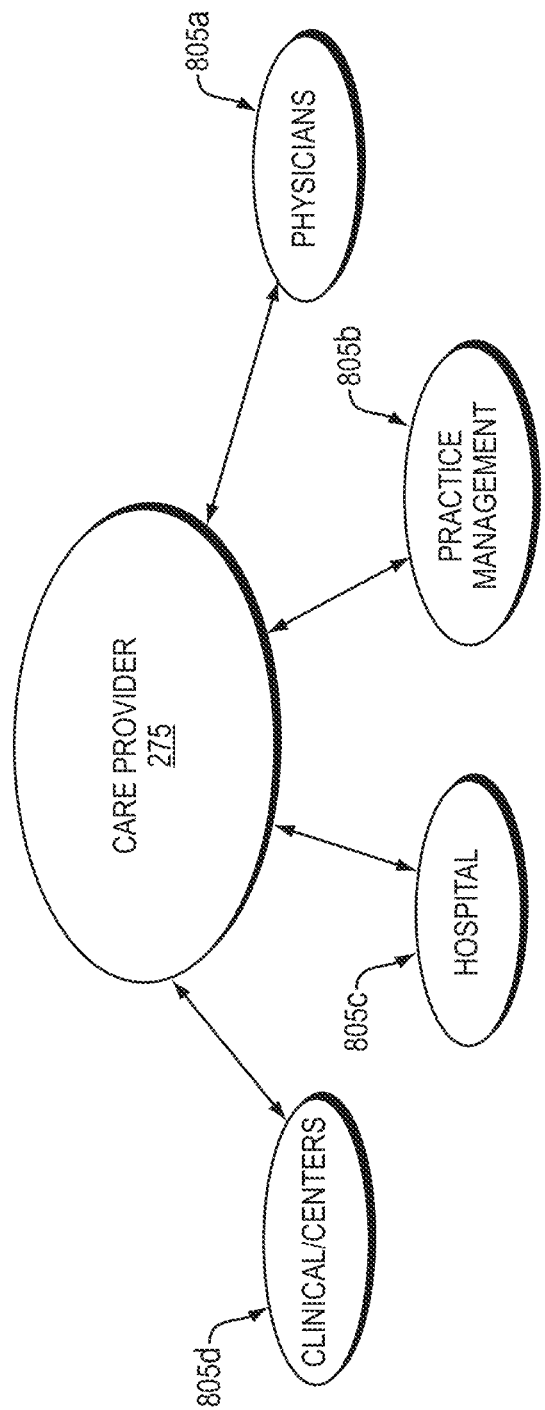

FIG. 8 shows an exemplary care provider component 275, including one or more units which provide patient care, as indicated by reference numerals 805a, 805b, . . . 805n. Any number "n" of units may be included in the provider component 275. In some embodiments, care providers may include physicians and/or physician groups 805a (e.g., primary care physicians (PCP) and specialists such as nephrologists), practice management systems 805b, hospitals 805c, and/or clinic/centers 805d, although additional or alternative care providers may also be envisioned. The integrated care system 220, 220' may send and receive information to and from the care providers for patient treatment. For example, the integrated care system 220, 220' may receive physician notes of patient examinations, hospitalization information, and the like, and may send calculated information and other determined factors based on other patient data received. For example, the integrated care system 220, 220' may send estimations and treatment recommendations to identify, reduce, avoid, and/or eliminate patient risk of aspects and/or effects of renal disease or renal disease treatments for providing treatment to a patient (e.g., identifying, treating for and minimizing risk of infections such as peritonitis) based on all received patient data and assessments performed thereon.

Figure 9:
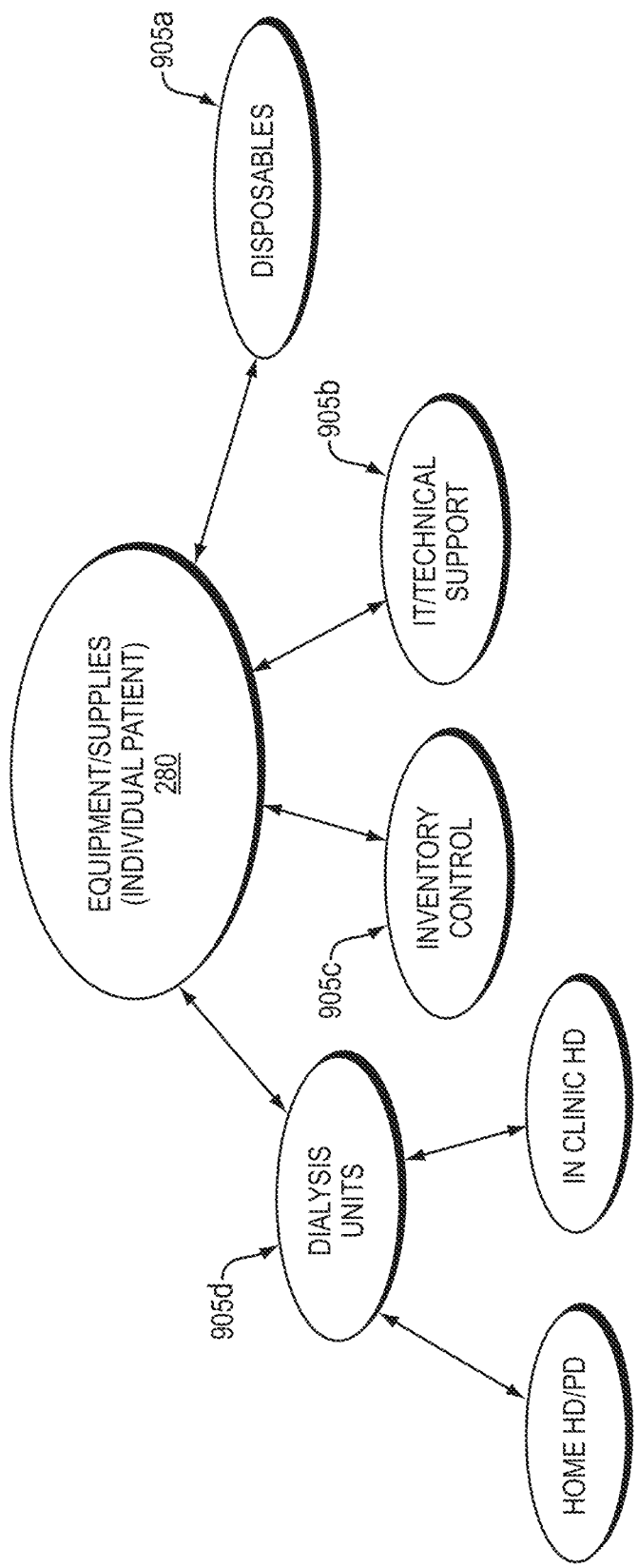

FIG. 9 shows an exemplary equipment and/or supplies component 280, for example, treatment supplies, for an individual patient, which may include any number "n" of services 905a, 905b, . . . 905n. In some embodiments, the integrated care system 220, 220' may send and receive information related to disposable medical equipment 905a, information technology (IT) technical support 905b, inventory control 905c, and/or dialysis units 905d or suite of dialysis machines in a clinic. As described above, many patients receive treatment at home, such as home dialysis, requiring an ongoing supply of disposable medical supplies for each treatment. Deliveries of supplies and/or dialysis equipment may be automatically monitored, replenished, and/or inventoried by the integrated care system 220, 220', to ensure proper machine functioning and a steady supply of materials and resources to ensure a patient receives all prescribed treatments.

Figure 10:
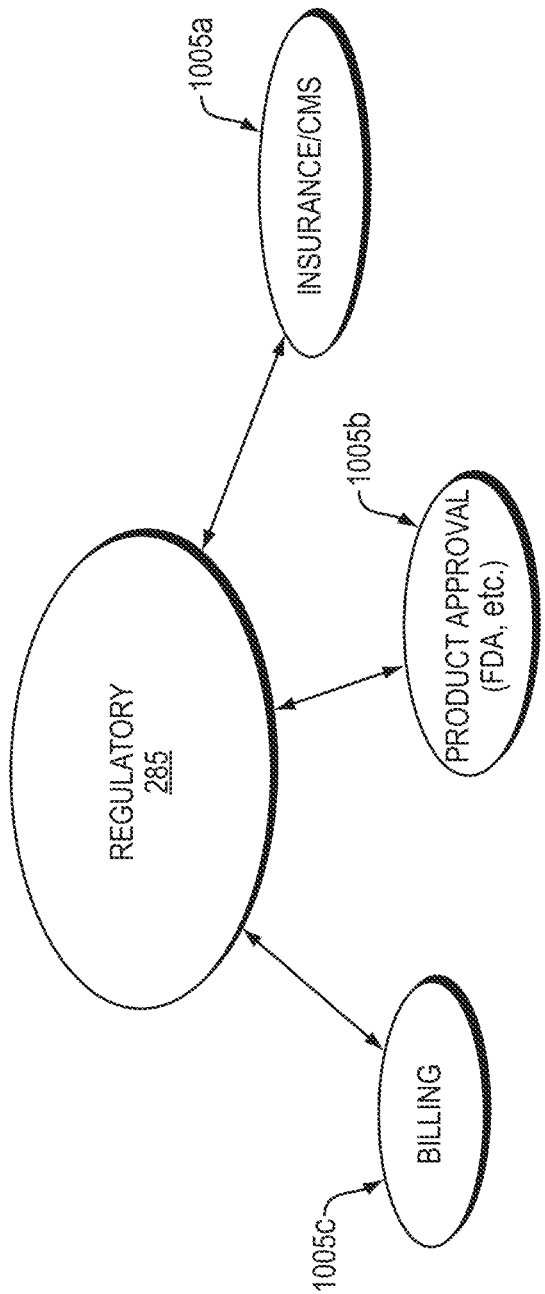

FIG. 10 shows an exemplary regulatory component 285, which may include any number "n" of services 1005a, 1005b, . . . 1005n related to governmental and regulatory requirements. For example, certain state and federal regulations and regulatory authorities may be involved in insurance and/or Centers for Medicaid and Medicare Services (CMS) 1005a, product approvals for the public (e.g., the Food and Drug Administration (FDA)) 1005b, and billing 1005c. The integrated care system 220, 220' may send and receive information to and from each of these units to ensure correct billing coding, regulatory approvals, and/or insurance payments.

Figure 11:
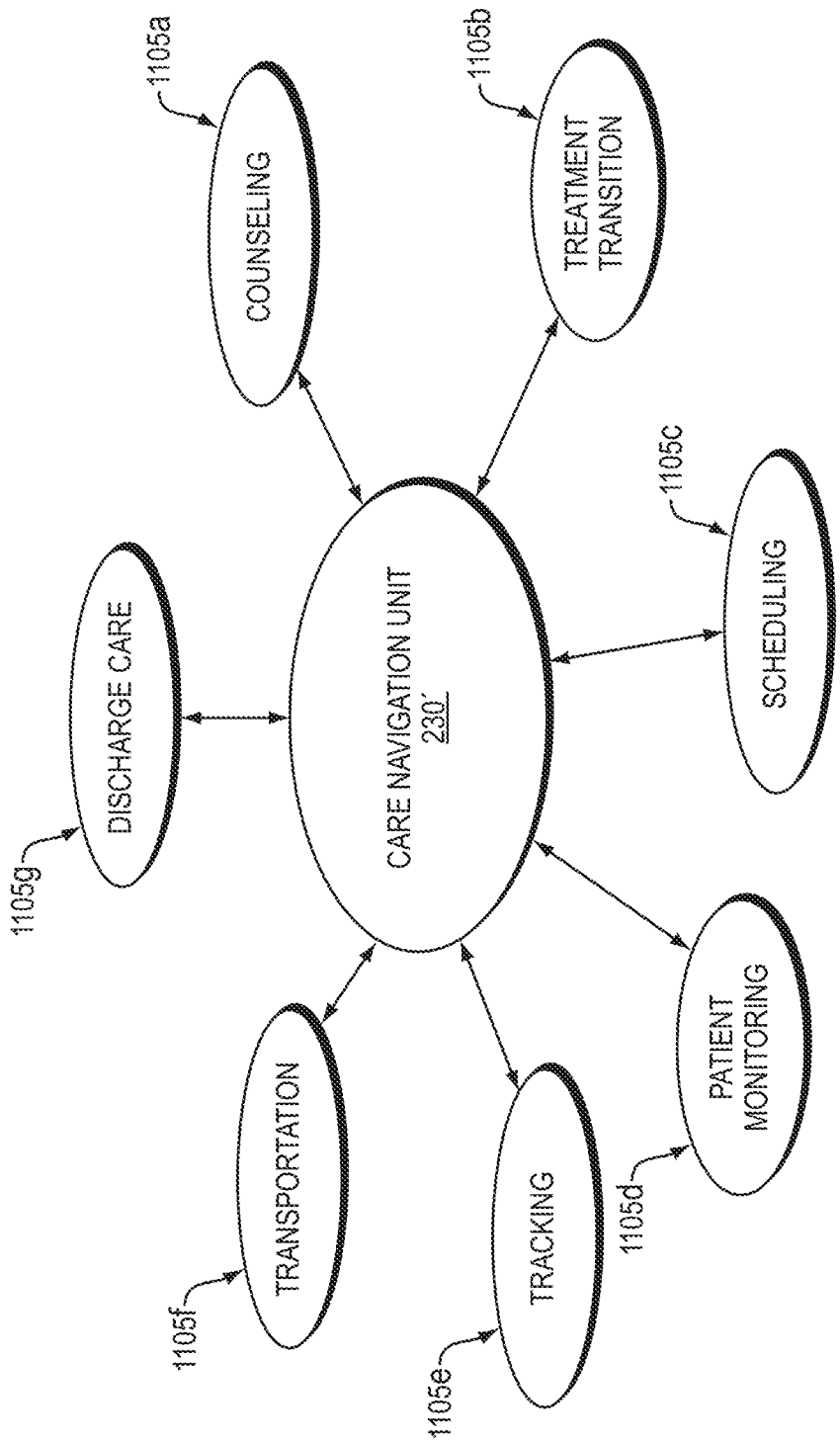
FIG. 11 is a diagram illustrating exemplary embodiments of care coordination components of systems providing coordinated healthcare, in accordance with the present disclosure.

A care navigation unit 230, 230', as introduced above, may oversee and coordinate patient care based on analysis and calculations by the integrated care system 220, 220' determined from data and information from any of the components 265, 270, 275, 280, 285, as well as the care coordination system 210'. For example, a care navigation unit 230', may coordinate care to patients to follow through on interventional treatments to address functional and/or cognitive patient impairment over time, improve comorbidity management, and help drive high-value care options and timing of treatment decisions to patients over time. As shown in FIG. 11, care navigation unit 230' may include different aspects of health care coordination as indicated by reference numerals 1105a, 1105b, . . . 1105n, including but not limited to counseling 1105a, treatment transition 1105b, scheduling 1105c, patient monitoring 1105d, tracking 1105e, transportation 1105f, and/or discharge care 1105g. For example, the integrated care system 220, 220' may determine that a patient requires transportation to/from a treatment center, and may automatically schedule transportation, e.g., public transportation, carpool, taxi, ride share, etc., so that the patient may not miss a scheduled treatment. Additionally, the integrated care system 220, 220' may send patient results to the relevant care providers, e.g., medical specialists, doctors, and/or nurses, for monitoring and/or treatment recommendations. Care navigation unit 230' may provide services to patients addressing their complete healthcare needs related to their kidney disease.

The care navigation unit 230, 230' may include treatment transition 1105*b*, for an integrated care system 220, 220' to coordinate patient care through progression of kidney disease. For example, a patient may initially be diagnosed with chronic kidney disease (CKD). Over time however, without interventional treatment (e.g., a kidney transplant) or improved kidney function, the patient may progress to end-stage renal disease (ESRD). As the patient's kidney disease progresses, the patient may need additional services, support, and/or health care, which may be overseen and/or managed under the care framework 200' by the care navigation unit 230' via the integrated care system 220, 220' and through a care framework of care coordination system 210, 210'.

Figure 3:
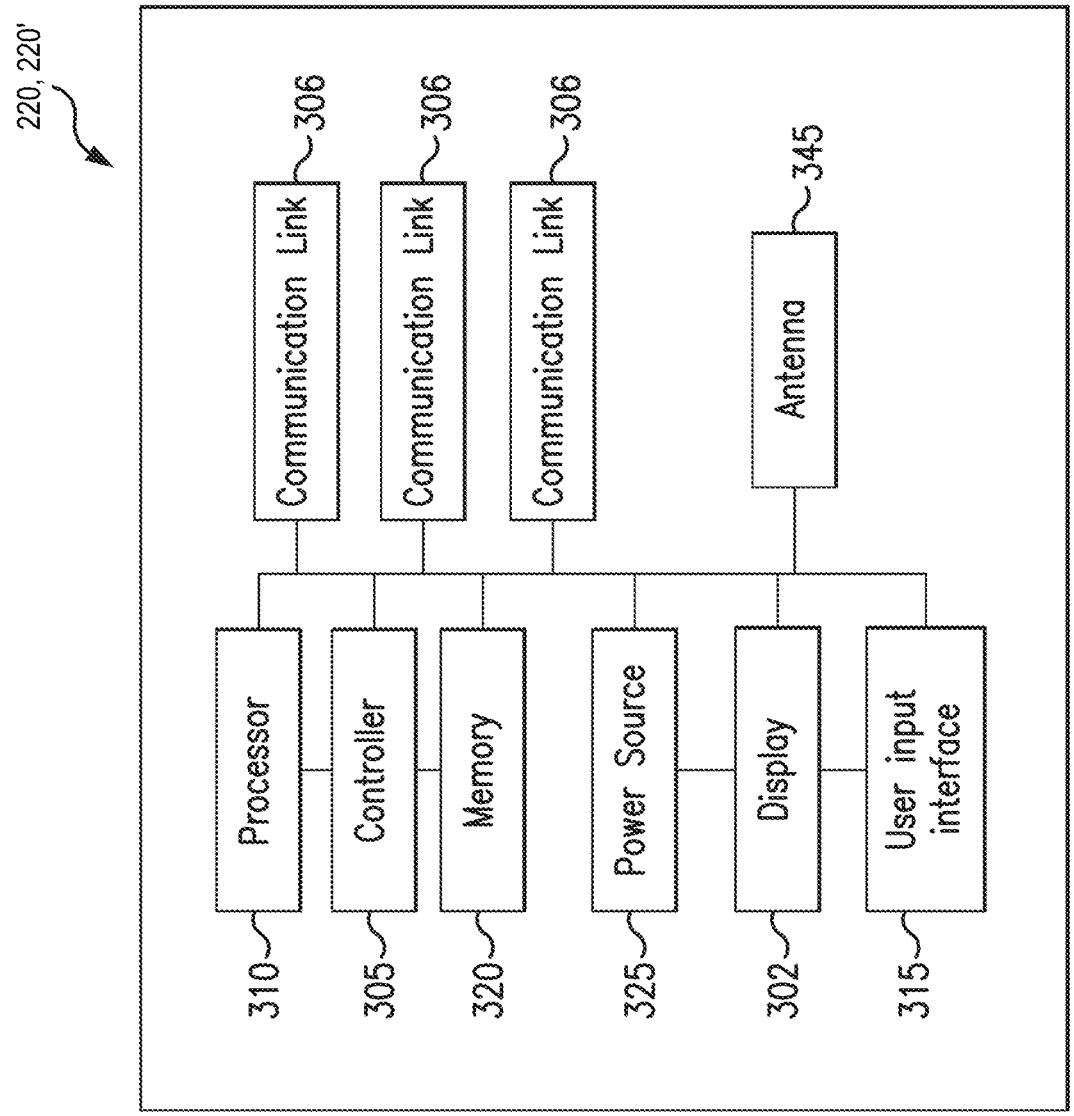
FIG. 3 is a block diagram illustrating an exemplary embodiment of an integrated care system in accordance with the present disclosure.

Referring now to FIG. 3, an integrated care system, such as integrated care system 220, 220', may include a controller 305, a processor 310, and a memory 320. The controller 305 may automatically control signals received and sent to other systems, e.g., the additional clinical systems, the external systems, and the practice management and billing system. Communication between the controller 305 and other systems may be bi-directional, whereby the systems may acknowledge control signals, and/or may provide information associated with the system and/or requested operations. Additionally, a user input interface 315 and display 302 may be disposed to receive and/or display input from a user, e.g., a patient or a medical professional such as a doctor, nurse, technician, or the like. Examples of the components that may be employed within the user input interface 315 include keypads, buttons, microphones, touch screens, gesture recognition devices, display screens, and speakers. In some embodiments, the integrated care system 220, 220' may be a server, a computer, or other device for storing and processing data, and controlling signals to other systems. A power source 325 may allow the integrated care system 220, 220' to receive power, and in some embodiments may be an independent power source.

The processor 310 may be configured to execute an operating system, which may provide platform services to application software, e.g., for operating the integrated care system 220, 220'. These platform services may include inter-process and network communication, file system management and standard database manipulation. One or more of many operating systems may be used, and examples are not limited to any particular operating system or operating system characteristic. In some examples, the processor 310 may be configured to execute a real-time operating system (RTOS), such as RTLinux, or a non-real time operating system, such as BSD or GNU/Linux. According to a variety of examples, the processor 310 may be a commercially available processor such as a processor manufactured by INTEL, AMD, MOTOROLA, and FREESCALE. However, the processor 310 may be any type of processor, multiprocessor or controller, whether commercially available or specially manufactured. For instance, according to one example, the processor 310 may include an MPC823 microprocessor manufactured by MOTOROLA.

The memory 320 may include a computer readable and writeable nonvolatile data storage medium configured to store non-transitory instructions and data. In addition, the memory 320 may include a processor memory that stores data during operation of the processor 310. In some examples, the processor memory includes a relatively high performance, volatile, random access memory such as dynamic random access memory (DRAM), static memory (SRAM), or synchronous DRAM. However, the processor memory may include any device for storing data, such as a non-volatile memory, with sufficient throughput and storage capacity to support the functions described herein. Further, examples are not limited to a particular memory, memory system, or data storage system.

The instructions stored on the memory 320 may include executable programs or other code that may be executed by the processor 310. The instructions may be persistently stored as encoded signals, and the instructions may cause the processor 310 to perform the functions described herein. The memory 320 may include information that is recorded, on or in, the medium, and this information may be processed by the processor 310 during execution of instructions. The memory 320 may also include, for example, data records, timing for treatment and/or operations, historic information, statistical information, and informational databases for treatments. A database may be stored in the memory 320 of the integrated care system 220, 220', and may be accessible by the processor 310 and controller 305. For example, historical data of patient information may be extracted from various databases in the integrated system 220, 220', including but not limited to patient lab results, treatment data, technician data during treatment (nurse notes), etc.

A patient population of data in the integrated care system 220, 220' may be analyzed for training a machine learning model for identifying patients at risk for developing an infection. The integrated care system 220, 220' may assess a large volume of patient data, e.g., the entire patient population receiving dialysis treatments in an at-home environment, e.g., by peritoneal dialysis. Extracted historical data may be used to train a machine learning model, e.g., for assessing factors leading to reported instances of peritonitis. For example, the machine learning model may identify characteristics of patients previously diagnosed with an infection such as peritonitis within a selected time period, and analyze patient lab results, treatment data, nurse notes, and the like, for commonalities that may contribute to their prediction. The machine learning model may further receive extracted historical data of patients that did not develop infections during a selected time period. In some embodiments, the machine learning model may exclude some patient data including outliers. In this manner, the machine learning model may be trained for identifying data associated with or indicative of an infection diagnosis and data associated with or indicative of no infection diagnosis. In some examples, an algorithm may be utilized for learning from and making predictions based on the historical data (either raw or pre-processed). For example, a gradient boosting framework, and/or an extreme gradient boosting tree algorithm may be utilized. Some examples implement XGBoost. The medium may be, for example, an optical disk, magnetic disk or flash memory, among others, and may be permanently affixed to, or removable from, the controller 305.

The integrated care system 220, 220' may include communication links 306, so that other systems may be connectable to the integrated care system 220, 220'. For example, additional clinical systems, external systems, and practice management and billing systems, may be connectable to the integrated care system 220, 220' to send and receive data and information associated with providing patient care. In some embodiments, the communication links 306 may be wireless, so that the systems may be remote, or the integrated care system 220, 220' and/or one or more of the systems 265, 270, 275, 280, 285, 230' may reside and operate in a cloud-based architecture.

One or more algorithms may utilize the model of historical data, to analyze newly input patient data as it is entered and/or gathered by the integrated care system 220, 220'. Algorithms may analyze the patient data based on the historical data to identify patients at risk for future infections. The integrated care system 220, 220' may further generate reports identifying the at-risk patients for follow-up treatment and/or retraining. For example, once a patient is identified as being at risk for developing an infection within a future time period, a medical professional may consult with the patient to understand the patient's at-home dialysis treatments and procedures, and/or supervise administration of dialysis to minimize the likelihood of developing or perpetuating an infection.

The integrated care system 220, 220' may also be wirelessly connectable via an antenna 345 for remote communication. For example, the integrated care system 220, 220' may determine one or more patient parameters by the controller 305, processor 310, and/or memory 320, and may access other patient parameters being stored by an outside system, e.g., in electronic medical records stored on a server or database in a location remote from the system or machine, or from labs or hospital information. It may be advantageous for the integrated care system 220, 220' to access other patient parameters that may otherwise be unknown or undeterminable in order to provide a complete care analysis of the patient. As described above, patient data may be sent to and/or accessible by the integrated care system 220, 220'. The controller 305, processor 310, and memory 320 may receive, store, and/or determine relevant demographic and laboratory values, or other data, for calculations.

The integrated care system 220, 220' may then use the calculations for determining a patient risk of developing an infection such as peritonitis. In some embodiments, as patient parameter information is updated, e.g., data points are included in the system, corresponding future or predicted patient parameters may be updated and adjusted accordingly. In embodiments, any number of variables may be extracted for determining a patient risk of developing an infection (see FIG. 1C). Additionally, notes, e.g., notes from medical professionals, may be included in determining patient risk. The one or more algorithms may generate a risk score of a patient developing an infection based on the extracted variables and the historical data, and in some embodiments may identify leading factors related to the generated risk score. By determining a patient's risk and reasons for developing an infection, medical professionals may be able to develop individualized patient interventions to minimize and/or eliminate the risk of developing an infection such as peritonitis, thereby allowing a patient to remain on the same dialysis modality (e.g., at-home peritoneal dialysis).

Figure 4:
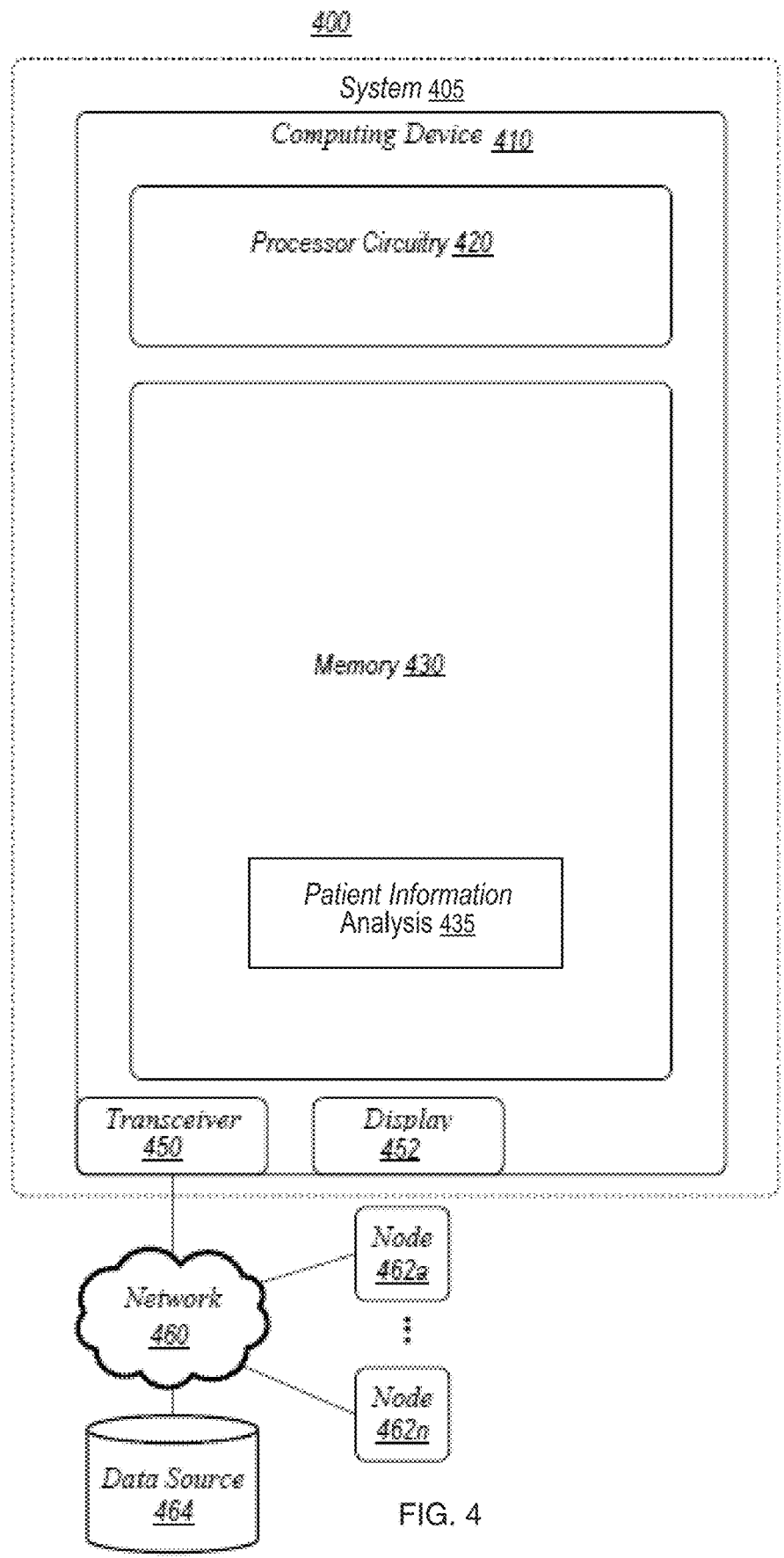
FIG. 4 is a block diagram illustrating an exemplary embodiment of an operating environment in accordance with the present disclosure.
Figure 5:
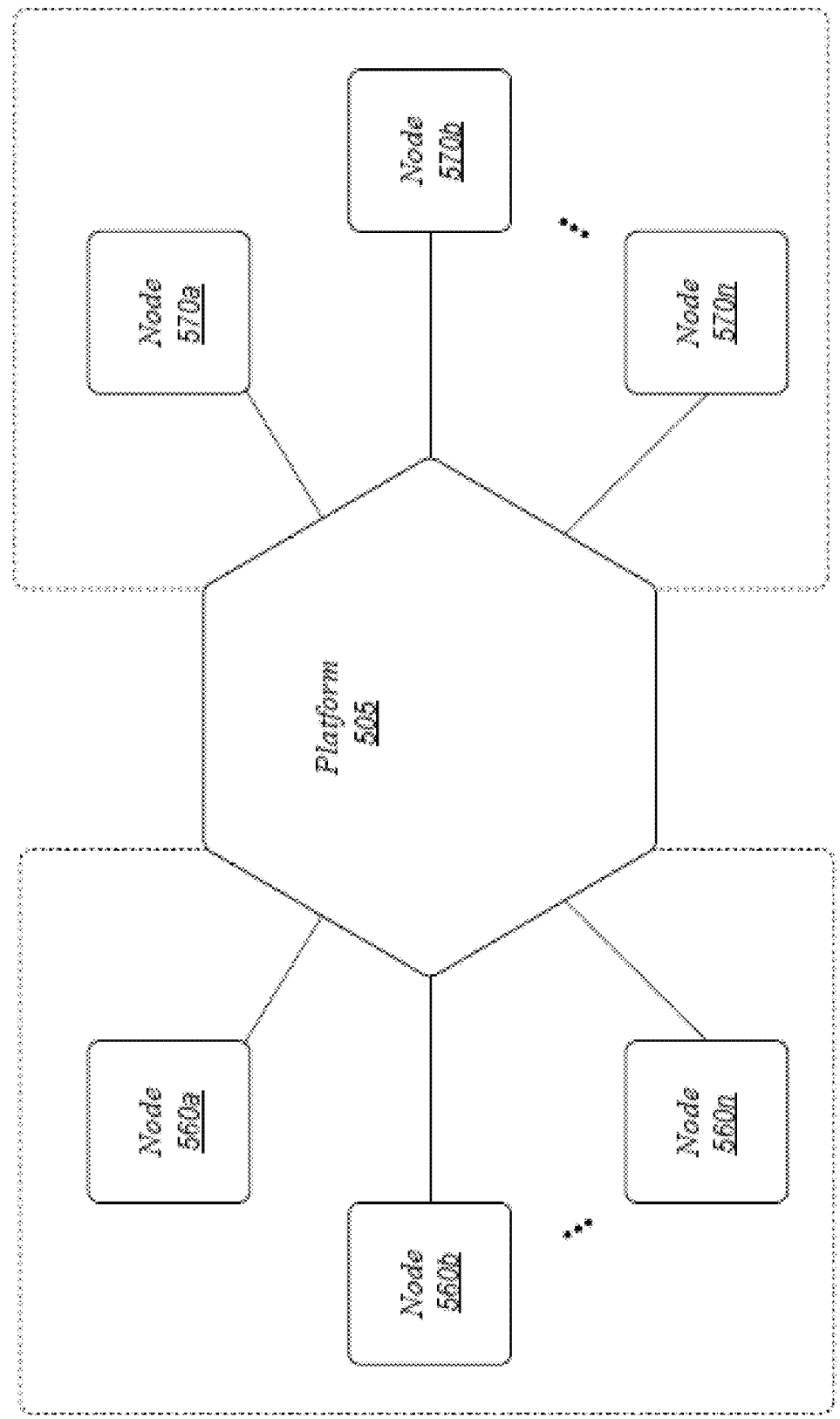
FIG. 5 is a block diagram illustrating an exemplary embodiment of another operating environment in accordance with the present disclosure.

Referring now to FIGS. 4-5, exemplary embodiments of an operating environment for a healthcare system (e.g., coordinated care framework 200, 200'), including integrated care system (care analysis and guidance system) 220, 220', are described. FIG. 4 illustrates an example of an operating environment 400 that may be representative of some embodiments. As shown in FIG. 4, operating environment 400 may include a system 405 operative for treating patients, e.g., patients having chronic illnesses. In various embodiments, the system 405 may include computing device 410. Computing device 410 may include processing circuitry 420, a memory unit 430, a transceiver 450, and/or a display 452. Processing circuitry 420 may be communicatively coupled to memory unit 430, transceiver 450, and/or display 452. It is understood that in some embodiments, system 405 may include the coordinated care framework 200, 200', and in some embodiments, the system 405 may include other systems and/or frameworks.

In some embodiments, computing device 410 may be connected to network 460 through transceiver 450. Network 460 may include nodes 462a-n, for example, remote computing devices, data sources 464, and/or the like.

Processing circuitry 420 may include and/or may access various logic for performing processes according to some embodiments. Processing circuitry 420, or portions thereof, may be implemented in hardware, software, or a combination thereof. As used in this application, the terms "logic," "component," "layer," "system," "circuitry," "decoder," "encoder," and/or "module" are intended to refer to a computer-related entity, either hardware, a combination of hardware and software, software, or software in execution, examples of which are provided by the exemplary computing architecture 1500 of FIG. 15. For example, a logic, circuitry, or a layer may be and/or may include, but are not limited to, a process running on a processor, a processor, a hard disk drive, multiple storage drives (of optical and/or magnetic storage medium), an object, an executable, a thread of execution, a program, a computer, hardware circuitry, integrated circuits, application specific integrated circuits (ASIC), programmable logic devices (PLD), digital signal processors (DSP), field programmable gate array (FPGA), a system-on-a-chip (SoC), memory units, logic gates, registers, semiconductor device, chips, microchips, chip sets, software components, programs, applications, firmware, software modules, computer code, combinations of any of the foregoing, and/or the like.

It is also understood that components of the processing circuitry 420 may be located within an accelerator, a processor core, an interface, an individual processor die, implemented entirely as a software application and/or the like.

Memory unit 430 may include various types of computer-readable storage media and/or systems in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In addition, memory unit 430 may include various types of computer-readable storage media in the form of one or more lower speed memory units, including an internal (or external) hard disk drive (HDD), a magnetic floppy disk drive (FDD), and an optical disk drive to read from or write to a removable optical disk (e.g., a CD-ROM or DVD), a solid state drive (SSD), and/or the like.

Memory unit 430 may store various information, e.g., one or more programs, to perform various functions identifying and treating patients with CKD and/or ESRD. In some embodiments, the memory 430 may include logic having application programming interfaces (APIs) and/or graphical user interfaces (GUIs) to read, write, and/or otherwise access information, such as via display 452, web interfaces, mobile application ("mobile applications," "mobile apps," or "apps"), and/or the like. In this manner, in some embodiments, an operator may search, visualize, read, add to, or otherwise access information associated with a patient population for identifying and treating CKD and/or ESRD.

In some embodiments, memory unit 430 may store various information associated with a patient population for identifying and treating CKD and/or ESRD. In some embodiments, information stored in memory unit 430 may be retrieved from and/or moved into a data source 464 including, without limitation, a hospital information management system (HIMS), laboratory information management system (LIMS), Health Information System (HIS), electronic medical records (EMR), a clinical trial database, and/or the like.

FIG. 5 illustrates an example of an operating environment 500 that may be representative of some embodiments. As shown in FIG. 5, operating environment 500 may include a platform 505, e.g., a healthcare exchange platform. In some embodiments, the platform 505 may be operative to provide for the exchange of clinical data and/or clinical trial information among interested entities. In various embodiments, the platform 505 may include an application platform operative for identifying a patient population and treating CKD and/or ESRD with services among nodes 560a-n and 570a-n. In exemplary embodiments, the platform 505 may be a software platform, suite, set of protocols, and/or the like provided to customers by a manufacturer and/or developer ("developer") associated with medical devices, medical care services, clinical research services, laboratory services, clinical trial services, and/or the like.

For example, a developer may provide the platform 505 as a data exchange interface for use by various entities, including government entities (for example, the FDA), and other stakeholders (for instance, pharmaceutical manufacturers, medical device manufacturers, and/or the like). An entity, such as a hospital, dialysis clinic, healthcare provider, government entity, regulatory entity, pharmaceutical manufacturer, medical device manufacturer, and/or the like providing and/or receiving clinical trial services via a node 570a-n provided by developer may use the platform 505 to implement processes according to some embodiments. Other entities may access the platform 505 via a GUI, such as a client application, web interface, mobile app, and/or the like, e.g., for performing functions associated with the memory. In some embodiments, at least a portion of the platform 505 may be hosted in a cloud computing environment.

Nodes 570a-n may be data producers for the memory and nodes 560a-n may be data consumers of the memory. For example, node 570a-n may include entities providing clinical data, model information, and/or the like used by the memory to generate, perform, and/or evaluate a patient population. Nodes 560a-n may include third-party applications, decision makers, analysis processes, regulators, and/or other data consumers that may be interested in the results of generating, performing, and/or evaluating the patient population. An entity may be both a data producer and a data consumer.

For example, node 560a may be care provider (node 560b) to provide treatment to a patient based on analysis of a patient population including medical records, laboratory data, pharmacy, and the like (node 570a). Data producers 570a-n may provide analytical data, according to permissions, to the platform 505, for example, in the form of records in a HIMS, LIMS, EMR, and/or the like. Data consumers 560a-n may access analytical data, according to permissions, via the platform 505 (for example, through HIMS, LIMS, EMR, and/or the like and/or local copies of such records).

In some embodiments, the platform 505 may operate according to a cloud-based model and/or an "as-a-Service" model. In this manner, the platform 505 may provide for a service that operates as a single, central platform that allows entities to access clinical data, model information, simulation results, and/or the like.

In some embodiments, one of the recommended treatments and/or services may be to alter or change a dialysis treatment prescription for a patient. As illustrated in FIGS. 12-14 and described below, a dialysis machine 1200, 1300, 1400, e.g., a dialysis machine such as a peritoneal dialysis machine or a hemodialysis machine, may be connected to the integrated care system 220, 220' for sending and receiving dialysis information to provide appropriate care to a patient. The hemodialysis machine may be located in a renal clinic, such as a kidney care clinic, dialysis clinic, or other third-party care provider. In some embodiments, the peritoneal dialysis machine and/or the hemodialysis machine may be home machines, e.g., treatment may be administered in a patient's home. As described above, an integrated care system may be applicable to other chronic illnesses, and may be connected to machines related to those illnesses, including but not limited to chronic kidney disease, or one or more of the other chronic diseases and conditions mentioned above.

Figure 12:
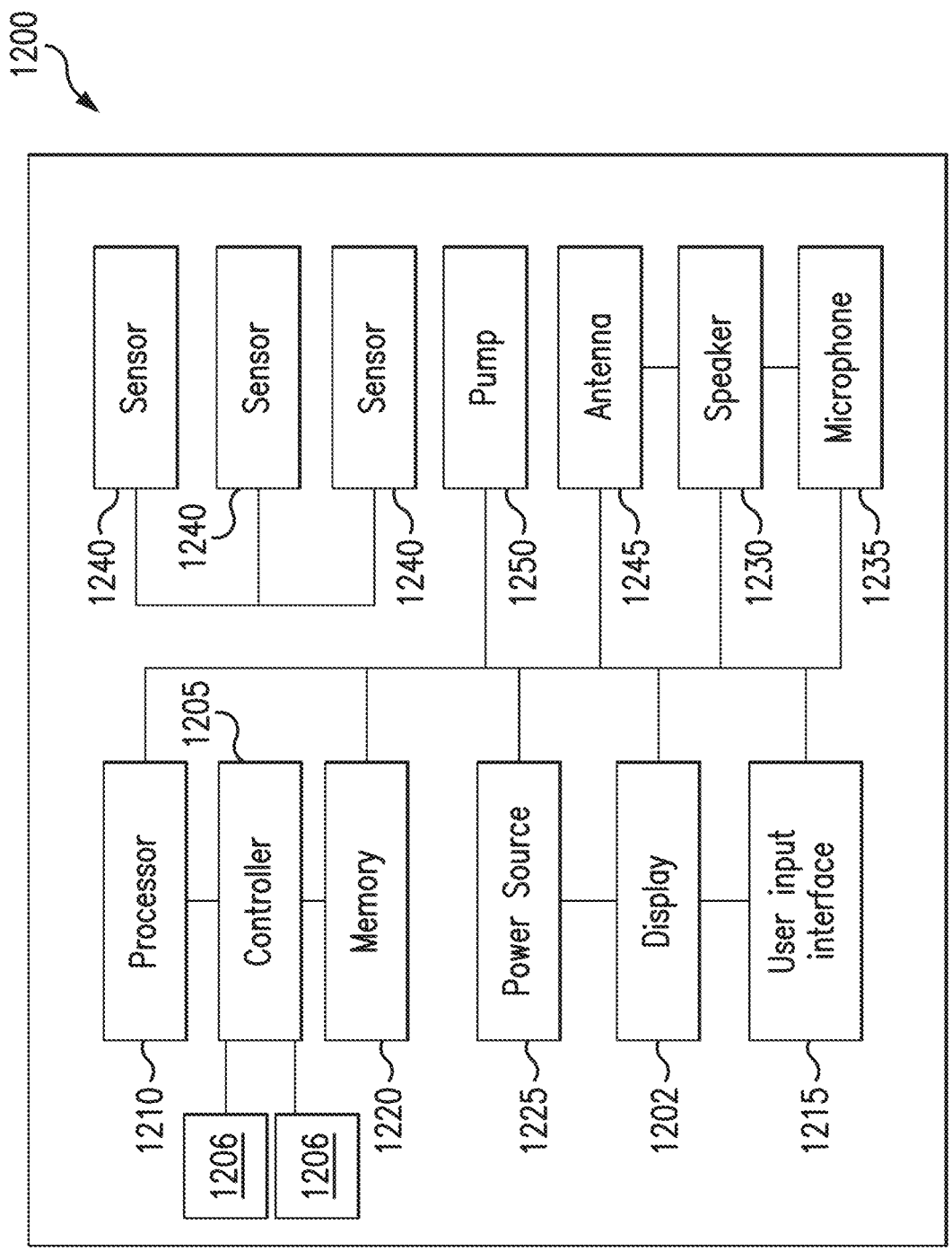
FIG. 12 illustrates a schematic of an exemplary embodiment of a dialysis machine.

Different dialysis modalities, as described with respect to FIGS. 12-14, may have some advantages over others. For example, hemodialysis administered in a clinic setting may be easier to maintain clean and sterilized areas for administering dialysis, so that the patient has a lower likelihood of developing an infection due to contamination. Dialysis machines are known for use in the treatment of renal disease. The two principal dialysis methods are hemodialysis (HD) and peritoneal dialysis (PD). During hemodialysis, the patient's blood is passed through a dialyzer of a hemodialysis machine while also passing dialysate through the dialyzer. A semi-permeable membrane in the dialyzer separates the blood from the dialysate within the dialyzer and allows diffusion and osmosis exchanges to take place between the dialysate and the blood stream. During peritoneal dialysis, the patient's peritoneal cavity is periodically infused with dialysate or dialysis solution. The membranous lining of the patient's peritoneum acts as a natural semi-permeable membrane that allows diffusion and osmosis exchanges to take place between the solution and the blood stream. Automated peritoneal dialysis machines, called PD cyclers, are designed to control the entire peritoneal dialysis process so that it can be performed at home, usually overnight, without clinical staff in attendance Referring to FIG. 12, a schematic of an exemplary embodiment of a dialysis machine 1200, and a controller 1205 in accordance with the present disclosure are shown. The machine 1200 may be a dialysis machine, e.g., a peritoneal dialysis machine or a hemodialysis machine, for performing a dialysis treatment on a patient (see FIGS. 12-14). The controller 1205 may automatically control execution of a treatment function during a course of dialysis treatment. For example, the controller 1205 may control dialysis treatment based on information received from the care analysis and guidance system 220, 220'. The controller 1205 may be operatively connected to sensors 1240 and deliver one or more signals to execute one or more treatment functions, or a course of treatment associated with various treatment systems. Although FIG. 12 illustrates the components integrated into the dialysis machine 1200, at least one of the controller 1205, processor 1210, and memory 1220 may be configured to be external and wired or wirelessly connected to the dialysis machine 1200, as an individual component of a dialysis system. In some embodiments the controller 1205, processor 1210 and memory 1220 may be remote to the dialysis machine and configured to communicate wirelessly.

In some embodiments, the controller 1205, processor 1210, and memory 1220 of the system or machine 1200, 1300, 1400, may receive signals from sensor 1240 indicating one or more patient parameters. Communication between the controller 1205 and the treatment system may be bi-directional, whereby the treatment system acknowledges control signals, and/or may provide state information associated with the treatment system and/or requested operations. For example, system state information may include a state associated with specific operations to be executed by the treatment system (e.g., trigger pump to deliver dialysate, trigger pumps and/or compressors to deliver filtered blood, and the like) and a status associated with specific operations (e.g., ready to execute, executing, completed, successfully completed, queued for execution, waiting for control signal, and the like).

The dialysis system or machine 1200, 1300, 1400, may also include at least one pump 1250 operatively connected to the controller 1205. The controller 1205 may also be operatively connected to one or more speakers 1230 and one or more microphones 1235 disposed in the system or machine 1200, 1300, 1400. The user input interface 1215 may include a combination of hardware and software components that allow the controller 1205 to communicate with an external entity, such as a patient or other user. These components may be configured to receive information from actions such as physical movement or gestures and verbal intonation. In embodiments, the components of the user input interface 1215 may provide information to external entities. Examples of the components that may be employed within the user input interface 1215 include keypads, buttons, microphones, touch screens, gesture recognition devices, display screens, and speakers.

As shown in FIG. 12, sensors 1240 may be included for detecting and monitoring one or more parameters and be operatively connected to at least the controller 1205, processor 1210, and memory 1220. The processor 1210 may be configured to execute an operating system, which may provide platform services to application software, e.g., for operating the dialysis machine 1200. These platform services may include inter-process and network communication, file system management and standard database manipulation. One or more of many operating systems may be used, and examples are not limited to any particular operating system or operating system characteristic. In some examples, the processor 1210 may be configured to execute a real-time operating system (RTOS), such as RTLinux, or a non-real time operating system, such as BSD or GNU/Linux. According to a variety of examples, the processor 1210 may be a commercially available processor such as a processor manufactured by INTEL, AMD, MOTOROLA, and FREESCALE. However, the processor 1210 may be any type of processor, multiprocessor or controller, whether commercially available or specially manufactured. For instance, according to one example, the processor 1210 may include an MPC823 microprocessor manufactured by MOTOROLA.

The memory 1220 may include a computer readable and writeable nonvolatile data storage medium configured to store non-transitory instructions and data. In addition, the memory 1220 may include a processor memory that stores data during operation of the processor 1210. In some examples, the processor memory includes a relatively high performance, volatile, random access memory such as dynamic random access memory (DRAM), static memory (SRAM), or synchronous DRAM. However, the processor memory may include any device for storing data, such as a non-volatile memory, with sufficient throughput and storage capacity to support the functions described herein. Further, examples are not limited to a particular memory, memory system, or data storage system.

The instructions stored on the memory 1220 may include executable programs or other code that may be executed by the processor 1210. The instructions may be persistently stored as encoded signals, and the instructions may cause the processor 1210 to perform the functions described herein. The memory 1220 may include information that is recorded, on or in, the medium, and this information may be processed by the processor 1210 during execution of instructions. The memory 1220 may also include, for example, specification of data records for user timing requirements, timing for treatment and/or operations, historic sensor information, and other databases and the like. The medium may, for example, be optical disk, magnetic disk or flash memory, among others, and may be permanently affixed to, or removable from, the controller 1205.

A pressure sensor may be included for monitoring fluid pressure of the system or machine 1200, 1300, 1400, although the sensors 1240 may also include any of a heart rate sensor, a respiration sensor, a temperature sensor, a weight sensor, a video sensor, a thermal imaging sensor, an electroencephalogram sensor, a motion sensor, audio sensor, an accelerometer, or capacitance sensor. It is appreciated that the sensors 1240 may include sensors with varying sampling rates, including wireless sensors. Based on data monitored by the sensors 1240, patient parameters such as a heart rate and a respiration rate may be determined by the controller 1205.

The controller 1205 may be disposed in the machine 1200, 1300, 1400, or may be coupled to the machine 1200, 1300, 1400, via a communication port or wireless communication links, shown schematically as communication element 1206. For example, the communication element 1206 may connect the dialysis machine 1200, 1300, 1400, to the care analysis and guidance system 220, 220', or another remote system such as an outside system or other clinical system. The dialysis machine 1200, 1300, 1400, may be connectable to the integrated care system 220, 220' via the communication element 1206 so that the controller 1205 may send and receive information and other signals to the care analysis and guidance system 220, 220'. As described above, the care analysis and guidance system 220, 220' may direct a prescribed dialysis treatment based on information received from other systems, e.g., outside systems, clinical systems, directly to the dialysis machine to ensure a patient receives the proper treatment. The dialysis machine may also send data and other information to the care analysis and guidance system 220, 220' so that if dialysis treatment requires adjustment, the care analysis and guidance system 220, 220' may ensure any changes will not adversely affect patient health.

As a component disposed within the machine 1200, 1300, 1400, the controller 1205 may be operatively connected to any one or more of the sensors 1240, pump 1250, pump heads 1404, 1406, and the like. The controller 1205 may communicate control signals or triggering voltages to the components of the system or machine 1200, 1300, 1400. As discussed, exemplary embodiments of the controller 1205 may include wireless communication interfaces. The controller 1205 may detect remote devices to determine if any remote sensors are available to augment any sensor data being used to evaluate the patient.

As shown in FIG. 12, a power source 1225 may be included to, for example, allow the machine to receive power, and in some embodiments may be an independent power source. A display 1202 may also be included. The display 1202 may function to provide information to the patient and the operator of the dialysis machine. For example, the display 1202 may illustrate information related to a dialysis treatment to be applied to the patient, including information related to a prescription. The dialysis machine may also be wirelessly connectable via an antenna 1245 for remote communication.

Figure 13A:
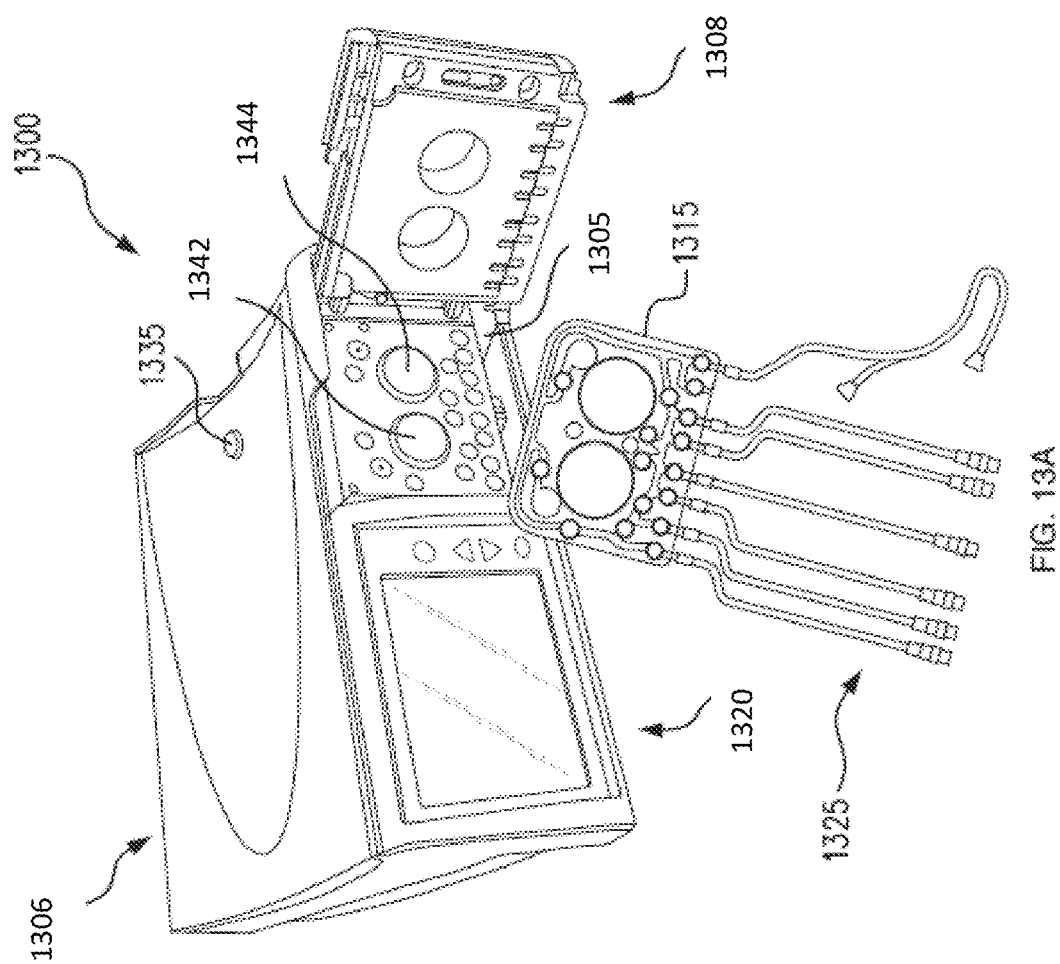
FIGS. 13A-13B illustrate an exemplary embodiment of a dialysis system in accordance with the present disclosure.
Figure 13B:
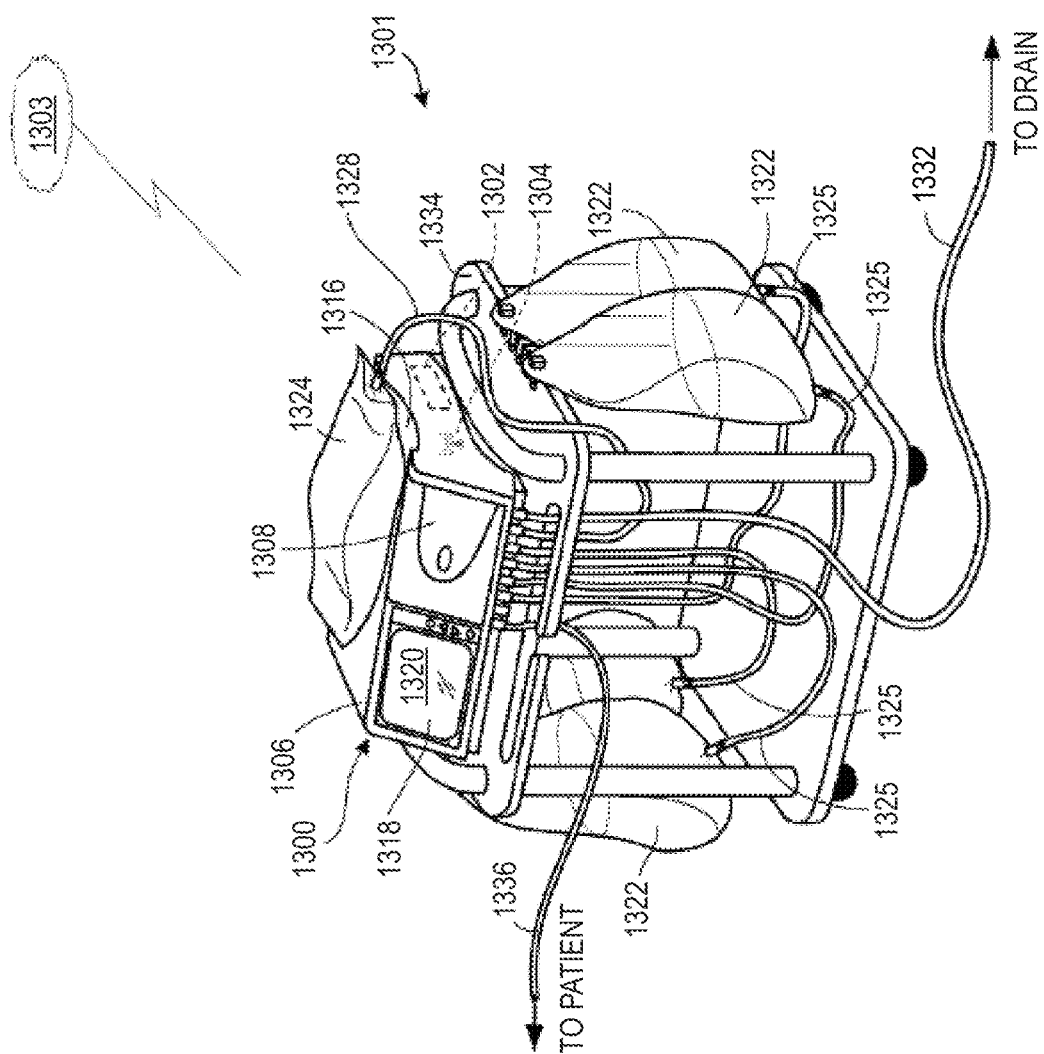

FIGS. 13A-13B show an example of a peritoneal dialysis (PD) system 1301, which is configured in accordance with an exemplary embodiment of the system described herein. In some implementations, the PD system 1301 may be a home PD system, e.g., a PD system configured for use at a patient's home. The dialysis system 1301 may include a dialysis machine 1300 (e.g., a peritoneal dialysis machine 1300, also referred to as a PD cycler) and in some embodiments the machine may be seated on a cart 1334.

The dialysis machine 1300 may include a housing 1306, a door 1308, and a cartridge interface including pump heads 1342, 1344 for contacting a disposable cassette, or cartridge 1315, where the cartridge 1315 is located within a compartment formed between the cartridge interface and the closed door 1308 (e.g., cavity 1305). Fluid lines 1325 may be coupled to the cartridge 1315 in a known manner, such as via a connector, and may further include valves for controlling fluid flow to and from fluid bags including fresh dialysate and warming fluid. In another embodiment, at least a portion of the fluid lines 1325 may be integral to the cartridge 1315. Prior to operation, a user may open the door 1308 to insert a fresh cartridge 1315, and to remove the used cartridge 1315 after operation.

The cartridge 1315 may be placed in the cavity 1305 of the machine 1300 for operation. During operation, dialysate fluid may be flowed into a patient's abdomen via the cartridge 1315, and spent dialysate, waste, and/or excess fluid may be removed from the patient's abdomen via the cartridge 1315. The door 1308 may be securely closed to the machine 1300. Peritoneal dialysis for a patient may include a total treatment of approximately 10 to 30 liters of fluid, where approximately 2 liters of dialysate fluid are pumped into a patient's abdomen, held for a period of time, e.g., about an hour, and then pumped out of the patient. This is repeated until the full treatment volume is achieved, and usually occurs overnight while a patient sleeps.

A heater tray 1316 may be positioned on top of the housing 1306. The heater tray 1316 may be any size and shape to accommodate a bag of dialysate (e.g., a 5 L bag of dialysate) for batch heating. The dialysis machine 1300 may also include a user interface such as a touch screen 1318 and control panel 1320 operable by a user (e.g., a caregiver or a patient) to allow, for example, set up, initiation, and/or termination of a dialysis treatment. In some embodiments, the heater tray 1316 may include a heating element 1335, for heating the dialysate prior to delivery into the patient.

Dialysate bags 1322 may be suspended from hooks on the sides of the cart 1334, and a heater bag 1324 may be positioned in the heater tray 1316. Hanging the dialysate bags 1322 may improve air management as air content may be disposed by gravity to a top portion of the dialysate bag 1322. Although four dialysate bags 1322 are illustrated in FIG. 13B, any number "n" of dialysate bags may be connectable to the dialysis machine 1300 (e.g., 1 to 5 bags, or more), and reference made to first and second bags is not limiting to the total number of bags used in a dialysis system 1301. For example, the dialysis machine may have dialysate bags 1322a, . . . 1322n connectable in the system 1301. In some embodiments, connectors and tubing ports may connect the dialysate bags 1322 and lines for transferring dialysate. Dialysate from the dialysate bags 1322 may be transferred to the heater bag 1324 in batches. For example, a batch of dialysate may be transferred from the dialysate bags 1322 to the heater bag 1324, where the dialysate is heated by the heating element 1335. When the batch of dialysate has reached a predetermined temperature (e.g., approximately 98°-100° F., 37° C.), the batch of dialysate may be flowed into the patient. The dialysate bags 1322 and the heater bag 1324 may be connected to the cartridge 1315 via dialysate bag lines or tubing 1325 and a heater bag line or tubing 1328, respectively. The dialysate bag lines 1325 may be used to pass dialysate from dialysate bags 1322 to the cartridge during use, and the heater bag line 1328 may be used to pass dialysate back and forth between the cartridge and the heater bag 1324 during use. In addition, a patient line 1336 and a drain line 1332 may be connected to the cartridge 1315. The patient line 1336 may be connected to a patient's abdomen via a catheter and may be used to pass dialysate back and forth between the cartridge and the patient's peritoneal cavity by the pump heads 1342, 1344 during use. The drain line 1332 may be connected to a drain or drain receptacle and may be used to pass dialysate from the cartridge to the drain or drain receptacle during use.

Although in some embodiments, dialysate may be batch heated as described above, in other embodiments, dialysis machines may heat dialysate by in-line heating, e.g., continuously flowing dialysate through a warmer pouch positioned between heating elements prior to delivery into a patient. For example, instead of a heater bag for batch heating being positioned on a heater tray, one or more heating elements may be disposed internal to the dialysis machine. A warmer pouch may be insertable into the dialysis machine via an opening. It is also understood that the warmer pouch may be connectable to the dialysis machine via tubing (e.g., tubing 1325), or fluid lines, via a cartridge. The tubing may be connectable so that dialysate may flow from the dialysate bags, through the warmer pouch for heating, and to the patient.

In such in-line heating embodiments, a warmer pouch may be configured so dialysate may continually flow through the warmer pouch (instead of transferred in batches for batch heating) to achieve a predetermined temperature before flowing into the patient. For example, in some embodiments the dialysate may continually flow through the warmer pouch at a rate between approximately 100-300 mL/min. Internal heating elements (not shown) may be positioned above and/or below the opening, so that when the warmer pouch is inserted into the opening, the one or more heating elements may affect the temperature of dialysate flowing through the warmer pouch. In some embodiments, the internal warmer pouch may instead be a portion of tubing in the system that is passed by, around, or otherwise configured with respect to, a heating element(s).

The touch screen 1318 and the control panel 1320 may allow an operator to input various treatment parameters to the dialysis machine 1300 and to otherwise control the dialysis machine 1300. In addition, the touch screen 1318 may serve as a display. The touch screen 1318 may function to provide information to the patient and the operator of the dialysis system 1301. For example, the touch screen 1318 may display information related to a dialysis treatment to be applied to the patient, including information related to a prescription.

The dialysis machine 1300 may include a processing module 1302 that resides inside the dialysis machine 1300, the processing module 1302 being configured to communicate with the touch screen 1318 and the control panel 1320. The processing module 1302 may be configured to receive data from the touch screen 1318 the control panel 1320 and sensors, e.g., weight, air, flow, temperature, and/or pressure sensors, and control the dialysis machine 1300 based on the received data. For example, the processing module 1302 may adjust the operating parameters of the dialysis machine 1300.

The dialysis machine 1300 may be configured to connect to a network 1303. The connection to network 1303 may be via a wired and/or wireless connection. The dialysis machine 1300 may include a connection component 1304 configured to facilitate the connection to the network 1303. The connection component 1304 may be a transceiver for wireless connections and/or other signal processor for processing signals transmitted and received over a wired connection. Other medical devices (e.g., other dialysis machines) or components may be configured to connect to the network 1303 and communicate with the dialysis machine 1300.

The user interface portion such as the touch screen 1318 and/or control panel 1320 may include one or more buttons for selecting and/or entering user information. The touch screen 1318 and/or control panel 1320 may be operatively connected to a controller (not shown) and disposed in the machine 1300 for receiving and processing the inputs to operate the dialysis machine 1300.

In some embodiments, the machine 1200, 1300, 1400 may wirelessly transmit (e.g., via a wireless Internet connection), alternatively or simultaneously or in coordination with sending information to the integrated care system 220, 220', information or alerts to a remote location, including but not limited to a doctor's office, hospital, call center, and technical support. For example, the machine 1200, 1300, 1400 may provide real time remote monitoring of machine operation and patient parameters. The memory 1220 of the machine 1200, may store data, or the machine 1200, 1300, 1400 may transmit data to a local or remote server at scheduled intervals. For example, the machine 1200, 1300, 1400, may send patient data to the integrated care system 220, 220', for use in calculating a risk score of a patient at risk for developing an infection (e.g., peritonitis).

FIG. 14 illustrates a diagram of an exemplary embodiment of a dialysis system 1400 in accordance with the present disclosure. The dialysis system 1400 may be configured to provide hemodialysis treatment to a patient 1401. Fluid reservoir 1402 may deliver fresh dialysate to a dialyzer 1404 via tubing 1403, and reservoir 1406 may receive spent dialysate once it has passed through the dialyzer 1404 via tubing 1405. A hemodialysis operation may filter particulates and/or contaminates from a patient's blood through a patient external filtration device, for example, a dialyzer 1404. As the dialysate is passed through the dialyzer 1404, so too unfiltered patient blood is passed into the dialyzer via tubing 1407 and filtered blood is returned to the patient via tubing 1409. Arterial pressure may be monitored via pressure sensor 1410, inflow pressure monitored via sensor 1418, and venous pressure monitored via pressure sensor 1414. An air trap and detector 1416 may ensure that air is not introduced into patient blood as it is filtered and returned to the patient 1401. The flow of blood and the flow of dialysate are controlled via respective pumps, including a blood pump 1412 and a fluid pump 1420. Heparin 1422, a blood thinner, may be used in conjunction with saline 1424 to ensure blood clots do not form or occlude blood flow through the system.

In some embodiments, the dialysis system 1400 may include a controller 1450, which may be similar to the controller 1205 described above with respect to dialysis machines 1200. The controller 1450 may be configured to monitor fluid pressure readings to identify fluctuations indicative of patient parameters, such as heart rate and/or respiration rate. In some embodiments, a patient heart rate and/or respiration rate may be determinable by the fluid pressure in the fluid flow lines and fluid bags. The controller 1450 may also be operatively connected to and/or communicate with additional sensors or sensor systems, although the controller 1450 may use any of the data available on the patient's biologic functions or other patient parameters.

Figure 15:
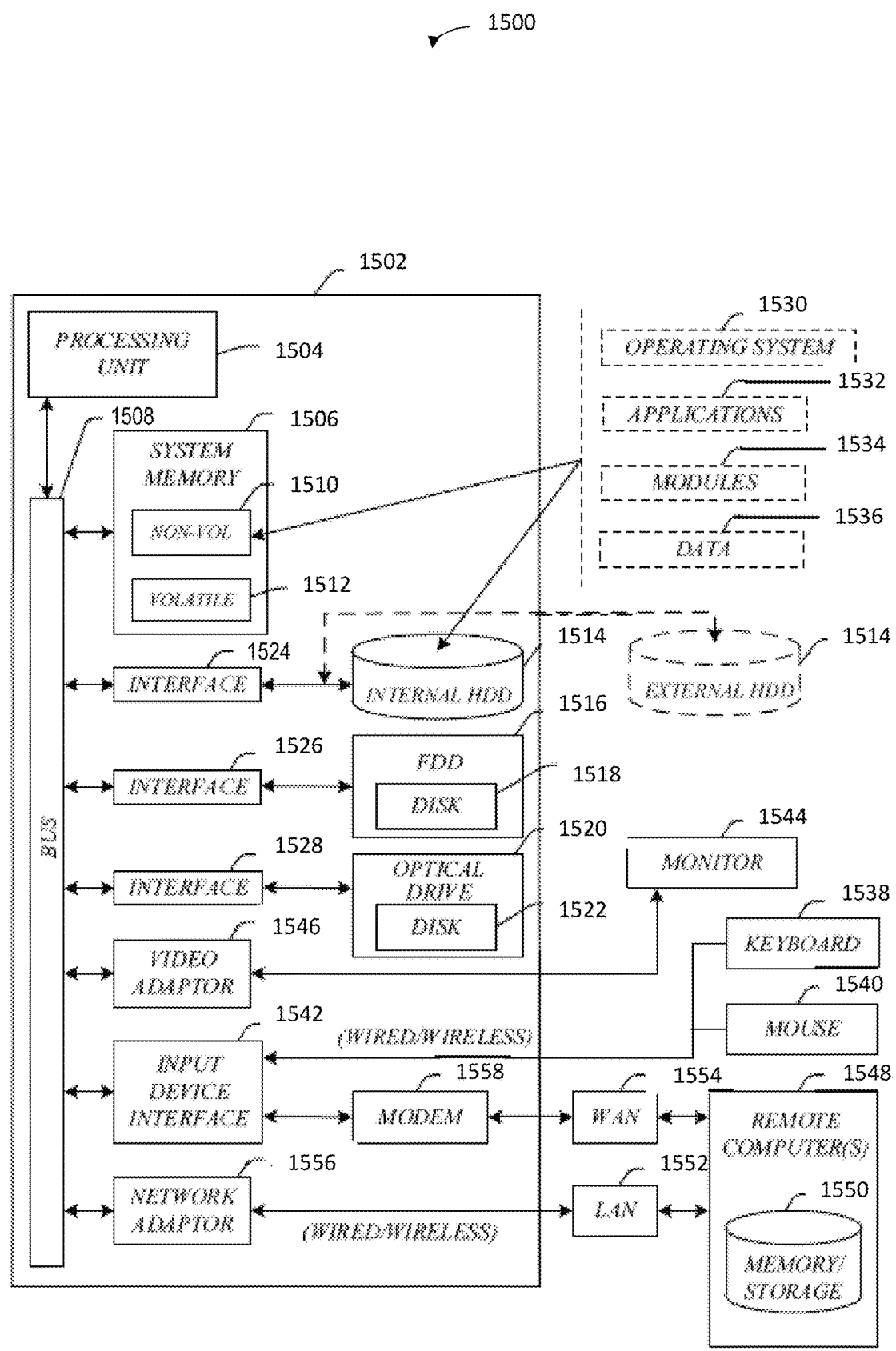
FIG. 15 is a block diagram illustrating an exemplary embodiment of a computing architecture in accordance with the present disclosure.

FIG. 15 illustrates an embodiment of an exemplary computing architecture 1500 suitable for implementing various embodiments as previously described. In various embodiments, the computing architecture 1500 may comprise or be implemented as part of an electronic device. In some embodiments, the computing architecture 1500 may be representative, for example, of computing device 410 and/or components of the platform 505 and/or integrated care system 220, 220'. The embodiments are not limited in this context.

As used in this application, the terms "system" and "component" and "module" are intended to refer to a computer-related entity, either hardware, a combination of hardware and software, software, or software in execution, examples of which are provided by the exemplary computing architecture 1500. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a server and the server can be a component. One or more components can reside within a process and/or thread of execution, and a component can be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to various signal lines. In such allocations, each message is a signal. Further embodiments, however, may alternatively employ data messages. Such data messages may be sent across various connections. Exemplary connections include parallel interfaces, serial interfaces, and bus interfaces.

The computing architecture 1500 includes various common computing elements, such as one or more processors, multi-core processors, co-processors, memory units, chipsets, controllers, peripherals, interfaces, oscillators, timing devices, video cards, audio cards, multimedia input/output (I/O) components, power supplies, and so forth. The embodiments, however, are not limited to implementation by the computing architecture 1500.

As shown in FIG. 15, the computing architecture 1500 comprises a processing unit 1504, a system memory 1506 and a system bus 1508. The processing unit 1504 can be any of various commercially available processors, including without limitation an AMD® Athlon®, Duron® and Opteron® processors; ARM® application, embedded and secure processors; IBM® and Motorola® DragonBall® and PowerPC® processors; IBM and Sony® Cell processors; Intel® Celeron®, Core (2) Duo®, Itanium®, Pentium®, Xeon®, and XScale® processors; and similar processors. Dual microprocessors, multi-core processors, and other multi-processor architectures may also be employed as the processing unit 1504.

The system bus 1508 provides an interface for system components including, but not limited to, the system memory 1506 to the processing unit 1504. The system bus 1508 can be any of several types of bus structure that may further interconnect to a memory bus (with or without a memory controller), a peripheral bus, and a local bus using any of a variety of commercially available bus architectures. Interface adapters may connect to the system bus 1508 via a slot architecture. Example slot architectures may include without limitation Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and the like.

The system memory 1506 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In the illustrated embodiment shown in FIG. 15, the system memory 1506 can include non-volatile memory 1510 and/or volatile memory 1512. A basic input/output system (BIOS) can be stored in the non-volatile memory 1510.

The computer 1502 may include various types of computer-readable storage media in the form of one or more lower speed memory units, including an internal (or external) hard disk drive (HDD) 1514, a magnetic floppy disk drive (FDD) 1516 to read from or write to a removable magnetic disk 1518, and an optical disk drive 1520 to read from or write to a removable optical disk 1522 (e.g., a CD-ROM or DVD). The HDD 1514, FDD 1516 and optical disk drive 1520 can be connected to the system bus 1508 by a HDD interface 1524, an FDD interface 1526 and an optical drive interface 1528, respectively. The HDD interface 1524 for external drive implementations can include at least one or both of Universal Serial Bus (USB) and IEEE 884 interface technologies.

The drives and associated computer-readable media provide volatile and/or nonvolatile storage of data, data structures, computer-executable instructions, and so forth. For example, a number of program modules can be stored in the drives and memory units 1510, 1512, including an operating system 1530, one or more application programs 1532, other program modules 1534, and program data 1536. In one embodiment, the one or more application programs 1532, other program modules 1534, and program data 1536 can include, for example, the various applications and/or components of system and/or apparatus 200, 200', 220, 220', 400, 500.

A user can enter commands and information into the computer 1502 through one or more wire/wireless input devices, for example, a keyboard 1538 and a pointing device, such as a mouse 1540. Other input devices may include microphones, infra-red (IR) remote controls, radio-frequency (RF) remote controls, game pads, stylus pens, card readers, dongles, finger print readers, gloves, graphics tablets, joysticks, keyboards, retina readers, touch screens (e.g., capacitive, resistive, etc.), trackballs, trackpads, sensors, styluses, and the like. These and other input devices are often connected to the processing unit 1504 through an input device interface 1542 that is coupled to the system bus 1508, but can be connected by other interfaces such as a parallel port, IEEE 894 serial port, a game port, a USB port, an IR interface, and so forth.

A monitor 1544 or other type of display device is also connected to the system bus 1508 via an interface, such as a video adaptor 1546. The monitor 1544 may be internal or external to the computer 1502. In addition to the monitor 1544, a computer typically includes other peripheral output devices, such as speakers, printers, and so forth.

The computer 1502 may operate in a networked environment using logical connections via wire and/or wireless communications to one or more remote computers, such as a remote computer 1548. The remote computer 1548 can be a workstation, a server computer, a router, a personal computer, portable computer, microprocessor-based entertainment appliance, a peer device or other common network node, and typically includes many or all of the elements described relative to the computer 1502, although, for purposes of brevity, only a memory/storage device 1550 is illustrated. The logical connections depicted include wire/wireless connectivity to a local area network (LAN) 1552 and/or larger networks, for example, a wide area network (WAN) 1554. Such LAN and WAN networking environments are commonplace in offices and companies, and facilitate enterprise-wide computer networks, such as intranets, all of which may connect to a global communications network, for example, the Internet.

When used in a LAN networking environment, the computer 1502 is connected to the LAN 1552 through a wire and/or wireless communication network interface or adaptor 1556. The adaptor 1556 can facilitate wire and/or wireless communications to the LAN 1552, which may also include a wireless access point disposed thereon for communicating with the wireless functionality of the adaptor 1556.

When used in a WAN networking environment, the computer 1502 can include a modem 1558, or is connected to a communications server on the WAN 1554, or has other means for establishing communications over the WAN 1554, such as by way of the Internet. The modem 1558, which can be internal or external and a wire and/or wireless device, connects to the system bus 1508 via the input device interface 1542. In a networked environment, program modules depicted relative to the computer 1502, or portions thereof, can be stored in the remote memory/storage device 1550. It will be appreciated that the network connections shown are exemplary and other means of establishing a communications link between the computers can be used.

The computer 1502 is operable to communicate with wire and wireless devices or entities using the IEEE 802 family of standards, such as wireless devices operatively disposed in wireless communication (e.g., IEEE 802.16 over-the-air modulation techniques). This includes at least Wi-Fi (or Wireless Fidelity), WiMax, and Bluetooth™ wireless technologies, among others. Thus, the communication can be a predefined structure as with a conventional network or simply an ad hoc communication between at least two devices. Wi-Fi networks use radio technologies called IEEE 802.11x (a, b, g, n, etc.) to provide secure, reliable, fast wireless connectivity. A Wi-Fi network can be used to connect computers to each other, to the Internet, and to wire networks (which use IEEE 802.3-related media and functions).

Some embodiments of the disclosed systems may be implemented, for example, using a storage medium, a computer-readable medium or an article of manufacture which may store an instruction or a set of instructions that, if executed by a machine (i.e., processor or microcontroller), may cause the machine to perform a method and/or operations in accordance with embodiments of the disclosure. In addition, a server or database server may include machine readable media configured to store machine executable program instructions. Such a machine may include, for example, any suitable processing platform, computing platform, computing device, processing device, computing system, processing system, computer, processor, or the like, and may be implemented using any suitable combination of hardware, software, firmware, or a combination thereof and utilized in systems, subsystems, components, or sub-components thereof. The computer-readable medium or article may include, for example, any suitable type of memory unit, memory device, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

Numerous specific details have been set forth herein to provide a thorough understanding of the embodiments. It will be understood by those skilled in the art, however, that the embodiments may be practiced without these specific details. In other instances, well-known operations, components, and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Unless specifically stated otherwise, it may be appreciated that terms such as "processing," "computing," "calculating," "determining," or the like, refer to the action and/or processes of a computer or computing system, or similar electronic computing device, that manipulates and/or transforms data represented as physical quantities (e.g., electronic) within the computing system's registers and/or memories into other data similarly represented as physical quantities within the computing system's memories, registers or other such information storage, transmission or display devices. The embodiments are not limited in this context.

It should be noted that the methods described herein do not have to be executed in the order described, or in any particular order. Moreover, various activities described with respect to the methods identified herein can be executed in serial or parallel fashion.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, an element or operation recited in the singular and proceeded with the word "a" or "an" should be understood as not excluding plural elements or operations, unless such exclusion is explicitly recited. Furthermore, references to "one embodiment" of the present disclosure are not intended to be interpreted as excluding the existence of additional embodiments that also incorporate the recited features.

To the extent used in this description and in the claims, a recitation in the general form of "at least one of [a] and [b]" should be construed as disjunctive. For example, a recitation of "at least one of [a], [b], and [c]" would include [a] alone, [b] alone, [c] alone, or any combination of [a], [b], and [c].

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes.

The invention claimed is:

1. A system for determining a patient's risk of developing an infection, the system comprising:
at least one computing device comprising:
a memory storing instructions; and
a processor coupled to the memory operative to, responsive to executing the instructions:
extract patient historical data from one or more databases corresponding to a pool of patients receiving at-home peritoneal dialysis treatment, the pool of patients comprising a first pool of patients previously diagnosed with an infection within a selected time period and a second pool of patients that did not develop an infection within the selected time period;
form a training set representative of at least a portion of the first pool of patients and a portion of the second pool of patients;
train one or more predictive models using the training set to determine factors associated with an infection diagnosis and to determine factors associated with no infection diagnosis;
analyze patient data of a patient via the one or more predictive models to determine:
a patient risk score for the patient to develop an infection within the selected time period, and
at least one reason associated with the patient risk score identifying leading factors for developing the infection; and
determine, responsive to patient risk score being over a predetermined threshold value, at least one individualized interventional treatment for the patient based on the patient risk score and the at least one reason to reduce the risk of the patient developing the infection.

2. The system of claim 1, wherein the one or more predictive models are arranged and configured to:
analyze the extracted historical patient data to identify patient characteristics common to patients having previous documented reports of infections; and
identify the patient characteristics in each of the patients in the pool of patients when generating the patient risk score for developing an infection within the selected time period.

3. The system of claim 2, wherein the one or more predictive models are arranged and configured to: analyze the extracted historical patient data to identify patient characteristics common to patients who have not had previous documented reports of infections.

4. The system of claim 1, wherein the one or more predictive models are arranged and configured to:
identify characteristics of patients previously diagnosed with an infection; and
analyze the extracted historical patient data against the characteristics for commonalities.

5. The system of claim 1, wherein the at least one individualized interventional treatment comprises at least one of:
transmitting a questionnaire to the patient to obtain additional information about the patient's administration of dialysis;
contacting the patient to determine appropriate interventions to aid in minimizing a risk of developing the infection;
contacting the patient for an assessment of the patient's dialysis treatment;
altering one or more conditions regarding the patient's administration of dialysis;
sending a medical professional for an in-home visual assessment of the patient's administration of dialysis; or
combinations thereof.

6. The system of claim 1, wherein the pool of patients comprises patients in a similar geographic area, patients assigned to a dialysis clinic, or a group of patients receiving care from an individual medical professional, or combinations thereof.

7. The system of claim 1, wherein the predetermined threshold value is determined by the one or more predictive models based on historical data.

8. The system of claim 1, wherein the extracted historical patient data comprises patient demographics, laboratory values, recorded information, physician notes, or treatment data, or combinations thereof.

9. The system of claim 8, wherein the patient demographics comprises gender, race, age, or marital status, or combinations thereof.

10. The system of claim 8, wherein the laboratory values comprise a patient's albumin level, a patient's calcium level, a patient's chloride level, a patient's creatinine level, or a patient's transferrin saturation (TSAT) level, or combinations thereof.

11. The system of claim 10, wherein the laboratory values comprise a time period over which a patient has been undergoing dialysis treatments, a time period over which a patient was last diagnosed with an infection, a total number of previous infections from a patient, or a distance of a patient's home to a dialysis facility, or combinations thereof.

12. The system of claim 1, wherein the selected time period is one month.

13. The system of claim 1, wherein the processor, responsive to executing the instructions, is further operative to analyze patient data of a plurality of patients via the one or more predictive models to determine:
a patient risk score for each of the plurality of patients to develop an infection within the selected time period, and
at least one reason associated with the patient risk score identifying leading factors for developing the infection,
wherein the plurality of patients includes the patient.

14. The system of claim 13, wherein the processor, responsive to executing the instructions, is further operative to determine at least one individualized interventional treatment for each patient of the plurality of patients with a patient risk score greater than the predetermined threshold value.

15. A method for determining a patient's risk of developing an infection, the method comprising:
extracting patient historical data from one or more databases corresponding to a pool of patients receiving at-home peritoneal dialysis treatment, the pool of patients comprising a first pool of patients previously diagnosed with an infection within a selected time period and a second pool of patients that did not develop an infection within the selected time period;
forming a training set representative of at least a portion of the first pool of patients and a portion of the second pool of patients;
training one or more predictive models using the training set to determine factors associated with an infection diagnosis and to determine factors associated with no infection diagnosis;

analyzing patient data of a patient via the one or more predictive models to determine:
- a patient risk score for the patient to develop an infection within the selected time period, and
- at least one reason associated with the patient risk score identifying leading factors for developing the infection; and administering, responsive to patient risk score being over a predetermined threshold value, at least one individualized interventional treatment to the patient based on the patient risk score and the at least one reason to reduce the risk of the patient developing the infection.

16. The method of claim 15, wherein the one or more predictive models are arranged and configured to:
- analyze the extracted historical patient data to identify patient characteristics common to patients having previous documented reports of infections; and
- identify the patient characteristics in each of the patients in the pool of patients when generating the patient risk score for developing an infection within a selected time period.

17. The method of claim 16, wherein the one or more predictive models are arranged and configured to: analyze the extracted historical patient data to identify patient characteristics common to patients who have not had previous documented reports of infections.

18. The method of claim 15, wherein the one or more predictive models are arranged and configured to:
- identify characteristics of patients previously diagnosed with an infection; and
- analyze the extracted historical patient data against the characteristics for commonalities.

19. The method of claim 15, wherein the at least one individualized interventional treatment comprises at least one of:
- transmitting a questionnaire to the patient to obtain additional information about the patient's administration of dialysis;
- contacting the patient to determine appropriate interventions to aid in minimizing a risk of developing the infection;
- contacting the patient for an assessment of the patient's dialysis treatment;
- altering one or more conditions regarding the patient's administration of dialysis;
- sending a medical professional for an in-home visual assessment of the patient's administration of dialysis; or
- combinations thereof.

20. The method of claim 15, wherein the pool of patients comprises patients in a similar geographic area, patients assigned to a dialysis clinic, or a group of patients receiving care from an individual medical professional, or combinations thereof.

21. The method of claim 15, wherein the predetermined threshold value is determined by the one or more predictive models based on historical data.

22. The method of claim 15, wherein the extracted historical patient data comprises patient demographics, laboratory values, recorded information, physician notes, or treatment data, or combinations thereof.

23. The method of claim 22, wherein the patient demographics comprises gender, race, age, or marital status, or combinations thereof.

24. The method of claim 22, wherein the laboratory values comprise a patient's albumin level, a patient's calcium level, a patient's chloride level, a patient's creatinine level, or a patient's transferrin saturation (TSAT) level, or combinations thereof.

25. The method of claim 24, wherein the laboratory values comprise a time period over which a patient has been undergoing dialysis treatments, a time period over which a patient was last diagnosed with an infection, a total number of previous infections from a patient, or a distance of a patient's home to a dialysis facility, or combinations thereof.

26. The method of claim 15, wherein the selected time period is one month.

27. The method of claim 15, comprising analyzing patient data of a plurality of patients via the one or more predictive models to determine:
- a patient risk score for each of the plurality of patients to develop an infection within the selected time period, and
- at least one reason associated with the patient risk score identifying leading factors for developing the infection, wherein the plurality of patients includes the patient.

28. The method of claim 27, comprising determining at least one individualized interventional treatment for each patient of the plurality of patients with a patient risk score greater than the predetermined threshold value.

* * * * *